United States Patent [19]
Griffin et al.

[11] Patent Number: 5,321,123
[45] Date of Patent: Jun. 14, 1994

[54] PROTEIN S POLYPEPTIDES AND ANTI-PEPTIDE ANTIBODIES THAT INHIBIT PROTEIN S BINDING TO C4B BINDING PROTEIN, DIAGNOSTIC SYSTEMS AND THERAPEUTIC METHODS

[75] Inventors: John H. Griffin, Del Mar; Jose A. Fernandez, La Jolla, both of Calif.

[73] Assignee: The Scripps Research Institute, La Jolla, Calif.

[21] Appl. No.: 907,190

[22] Filed: Jul. 1, 1992

Related U.S. Application Data

[63] Continuation-in-part of Ser. No. 724,746, Jul. 2, 1991, abandoned.

[51] Int. Cl.$^5$ .................. C07K 7/00; C07K 7/06; C07K 7/08; C07K 7/10
[52] U.S. Cl. .................. 530/300; 530/324; 530/325; 530/327; 530/328; 530/329; 530/830; 436/501; 435/7.93
[58] Field of Search .................. 530/300, 829, 830; 514/2

[56] References Cited

U.S. PATENT DOCUMENTS

4,361,509 11/1982 Zimmerman et al.

OTHER PUBLICATIONS

Dahlbuck et al., J. Biol. Chem. 261:5114–5115, 1986.
Hoskins et al., PNAS, 84:349–353, 1987.
Walker et al., J. Biol. Chem. 264:17645–17648, 1989.
Baker et al., "Vitamin K-Dependent Protein S is Similar to Rat Androgen-Binding Protein", in *Biochem. J.*, 243:293–296 (1987).
Comp, et al., "An Abnormal Plasma Distribution of Protein S Occurs in Functional Protein S Deficiency", in *Blood*, 67:504–508 (1986).
Dahlbäck, et al., "Characterization of Functionally Important Domains in Human Vitamin K-Dependent Protein S Using Monoclonal Antibodies", in *J. Biol. Chem.*, 265: 8127–8135 (1990).
Edson, et al., "Laboratory Diagnosis of Inherited Protein S Deficiency", in *Am. J. Clin. Path.*, 94: 176–186 (1990).
Gershagen, et al., "A cDNA Coding for Human Sex Hormone Binding Globulin-Homology to Vitamin K-dependent Protein S", in *PEBS Letters*, 220: 129–135 (1987).
Hessing, et al., "The Interaction Between Complement Component C4b-Binding Protein and the Vitamin K-Dependent Protein S Forms a Link Between Blood Coagulation and the Complement System", in *Biochem J.*, 277: 581–592 (1991).
Laurrel, "Antigen-Antibody Crossed Electrophoresis", in *Anal. Biochem.*, 10: 358–361 (1965).
Malm, et al., "Inhibition of Human Vitamin-K-Dependent Protein -S-Cofactor Activity by a Monoclonal Antibody Specific for a $Ca^{2+}$-Dependent Epitope", in Eur. J. Biochem., 165:39–45 (1987).
Nukatsuka, et al., "Characterization of the Interaction Between Human Protein S and C4b-Binding Protein (C4bp)", in *J. Biochem.*, 102: 599–605 (1987).
Stenflo, et al., "$\beta$-Hydroxyasparagine in Domains Homologous to the Epidermal Growth Factor Precursor in Vitamin-K-Dependent Protein S", in *Proc. Natl. Acad. Sci., USA*, 84: 368–372 (1987).
Weinstein, et al., "Enhancement of Rabbit Protein S Anticoagulant Cofactor Activity In Vivo by Modulation of the Protein S", in *J. Clin. Invest.*, 86: 1928–2935 (1990).
Schwartz, et al., "Plasma Protein S Deficiency in Familial Thrombotic Disease", *Blood*, 64: 1297–1300 (1984).

*Primary Examiner*—Christine M. Nucker
*Assistant Examiner*—Chris Dubrule
*Attorney, Agent, or Firm*—Douglas A. Bingham; Thomas Fitting; April C. Logan

[57] ABSTRACT

The invention describes protein S polypeptides and anti-PS antibodies capable of inhibiting the binding of proteins to C4BP. The peptides and antibodies are useful in diagnostic methods and systems for purifying or detecting free protein S. In addition, the polypeptides are useful in therapeutic methods as an anti-coagulant.

4 Claims, 5 Drawing Sheets

Normal Plasma

Mab56-Adsorbed Plasma

↑ C4BP:PS Complex  ↑ Free PS 1 2 3

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 635 amino acids
( B ) TYPE: amino acid
( D ) TOPOLOGY: unknown ( i i ) MOLECULE TYPE: protein ( x i ) SEQUENCE DESCRIPTION: SEQ ID NO:1:

```
Ala  Asn  Ser  Leu  Leu  Glu  Glu  Thr  Lys  Gln  Gly  Asn  Leu  Glu  Arg  Glu
 1                  5                           10                          15

Cys  Ile  Glu  Glu  Leu  Cys  Asn  Lys  Glu  Glu  Ala  Arg  Glu  Val  Phe  Glu
             20                          25                          30
```

```
Asn Asp Pro Glu Thr Asp Tyr Phe Tyr Pro Lys Tyr Leu Val Cys Leu
         35                  40              45

Arg Ser Phe Gln Thr Gly Leu Phe Thr Ala Ala Arg Gln Ser Thr Asn
         50              55              60

Ala Tyr Pro Asp Leu Arg Ser Cys Val Asn Ala Ile Pro Asp Gln Cys
65               70              75                          80

Ser Pro Leu Pro Cys Asn Glu Asp Gly Tyr Met Ser Cys Lys Asp Gly
                85              90              95

Lys Ala Ser Phe Thr Cys Thr Cys Lys Pro Gly Trp Gln Gly Glu Lys
            100             105             110

Cys Glu Phe Asp Ile Asn Glu Cys Lys Asp Pro Ser Asn Ile Asn Gly
            115             120             125

Gly Cys Ser Gln Ile Cys Asp Asn Thr Pro Gly Ser Tyr His Cys Ser
    130             135             140

Cys Lys Asn Gly Phe Val Met Leu Ser Asn Lys Lys Asp Cys Lys Asp
145             150             155                         160

Val Asp Glu Cys Ser Leu Lys Pro Ser Ile Cys Gly Thr Ala Val Cys
                165             170                         175

Lys Asn Ile Pro Gly Asp Phe Glu Cys Glu Cys Pro Glu Gly Tyr Arg
            180             185             190

Tyr Asn Leu Lys Ser Lys Ser Cys Glu Asp Ile Asp Glu Cys Ser Glu
        195             200             205

Asn Met Cys Ala Gln Leu Cys Val Asn Tyr Pro Gly Gly Tyr Thr Cys
    210             215             220

Tyr Cys Asp Gly Lys Lys Gly Phe Lys Leu Ala Gln Asp Gln Lys Ser
225             230             235                         240

Cys Glu Val Val Ser Val Cys Leu Pro Leu Asn Leu Asp Thr Lys Tyr
                245             250             255

Glu Leu Leu Tyr Leu Ala Glu Gln Phe Ala Gly Val Val Leu Tyr Leu
            260             265             270

Lys Phe Arg Leu Pro Glu Ile Ser Arg Phe Ser Ala Glu Phe Asp Phe
        275             280             285

Arg Thr Tyr Asp Ser Glu Gly Val Ile Leu Tyr Ala Glu Ser Ile Asp
    290             295             300

His Ser Ala Trp Leu Leu Ile Ala Leu Arg Gly Gly Lys Ile Glu Val
305             310             315                         320

Gln Leu Lys Asn Glu His Thr Ser Lys Ile Thr Thr Gly Gly Asp Val
            325             330             335

Ile Asn Asn Gly Leu Trp Asn Met Val Ser Val Glu Glu Leu Glu His
            340             345             350

Ser Ile Ser Ile Lys Ile Ala Lys Glu Ala Val Met Asp Ile Asn Lys
        355             360             365

Pro Gly Pro Leu Phe Lys Pro Glu Asn Gly Leu Leu Glu Thr Lys Val
    370             375             380

Tyr Phe Ala Gly Phe Pro Arg Lys Val Glu Ser Glu Leu Ile Lys Pro
385             390             395                         400

Ile Asn Pro Arg Leu Asp Gly Cys Ile Arg Ser Trp Asn Leu Met Lys
            405             410             415

Gln Gly Ala Ser Gly Ile Lys Glu Ile Ile Gln Glu Lys Gln Asn Lys
            420             425             430

His Cys Leu Val Thr Val Glu Lys Gly Ser Tyr Tyr Pro Gly Ser Gly
        435             440             445

Ile Ala Gln Phe His Ile Asp Tyr Asn Asn Val Ser Ser Ala Glu Gly
    450             455             460
```

```
Trp His Val Asn Val Thr Leu Asn Ile Arg Pro Ser Thr Gly Thr Gly
465                 470                 475                 480

Val Met Leu Ala Leu Val Ser Gly Asn Asn Thr Val Pro Phe Ala Val
                485                 490                 495

Ser Leu Val Asp Ser Thr Ser Glu Lys Ser Gln Asp Ile Leu Leu Ser
                500                 505                 510

Val Glu Asn Thr Val Ile Tyr Arg Ile Gln Ala Leu Ser Leu Cys Ser
            515                 520                 525

Asp Gln Gln Ser His Leu Glu Phe Arg Val Asn Arg Asn Asn Leu Glu
        530                 535                 540

Leu Ser Thr Pro Leu Lys Ile Glu Thr Ile Ser His Glu Asp Leu Gln
545                 550                 555                 560

Arg Gln Leu Ala Val Leu Asp Lys Ala Met Lys Ala Lys Val Ala Thr
                565                 570                 575

Tyr Leu Gly Gly Leu Pro Asp Val Pro Phe Ser Ala Thr Pro Val Asn
            580                 585                 590

Ala Phe Tyr Asn Gly Cys Met Glu Val Asn Ile Asn Gly Val Gln Leu
        595                 600                 605

Asp Leu Asp Glu Ala Ile Ser Lys His Asn Asp Ile Arg Ala His Ser
        610                 615                 620

Cys Pro Ser Val Trp Lys Lys Thr Lys Asn Ser
625                 630                 635
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:2:

```
Ser Gly Ile Lys Glu Ile Ile Gln Glu Lys Gln Asn Lys His Ser
1               5                   10                  15
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:3:

```
Ser Gly Val Lys Glu Ile Ile Gln Glu Lys Gln Asn Lys His Ser
1               5                   10                  15
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:4:

```
Asp Ile Arg Ser Trp Asn Leu Met Lys Gln Gly Ala Ser Gly Ile
1               5                   10                  15
```

( 2 ) INFORMATION FOR SEQ ID NO:5:

( i ) SEQUENCE CHARACTERISTICS:

(A) LENGTH: 15 amino acids
(B) TYPE: amino acid
(D) TOPOLOGY: unknown (ii) MOLECULE TYPE: peptide (xi) SEQUENCE DESCRIPTION: SEQ ID NO:5:

Ser Pro Glu Gly Tyr Arg Tyr Asn Leu Lys Ser Lys Ser Ser Glu
 1           5                  10                 15

(2) INFORMATION FOR SEQ ID NO:6:

(i) SEQUENCE CHARACTERISTICS:
    (A) LENGTH: 15 amino acids
    (B) TYPE: amino acid
    (D) TOPOLOGY: unknown (ii) MOLECULE TYPE: peptide (xi) SEQUENCE DESCRIPTION: SEQ ID NO:6:

Ile Asn Gly Val Gln Leu Asp Leu Asp Glu Ala Ile Ser Lys Cys
 1           5                  10                 15

(2) INFORMATION FOR SEQ ID NO:7:

(i) SEQUENCE CHARACTERISTICS:
    (A) LENGTH: 15 amino acids
    (B) TYPE: amino acid
    (D) TOPOLOGY: unknown (ii) MOLECULE TYPE: peptide (xi) SEQUENCE DESCRIPTION: SEQ ID NO:7:

Arg Ala His Ser Cys Pro Ser Val Trp Lys Lys Thr Lys Asn Cys
 1           5                  10                 15

(2) INFORMATION FOR SEQ ID NO:8:

(i) SEQUENCE CHARACTERISTICS:
    (A) LENGTH: 15 amino acids
    (B) TYPE: amino acid
    (D) TOPOLOGY: unknown (ii) MOLECULE TYPE: peptide (xi) SEQUENCE DESCRIPTION: SEQ ID NO:8:

Ser Asn Lys Thr Lys Lys Trp Val Ser Pro Ser Ser His Ala Arg
 1           5                  10                 15

(2) INFORMATION FOR SEQ ID NO:9:

(i) SEQUENCE CHARACTERISTICS:
    (A) LENGTH: 14 amino acids
    (B) TYPE: amino acid
    (D) TOPOLOGY: unknown (ii) MOLECULE TYPE: peptide (ix) FEATURE:
    (A) NAME/KEY: Region
    (B) LOCATION: 3
    (D) OTHER INFORMATION: /note="Where X is Ile or Val,
        preferably Ile."

(xi) SEQUENCE DESCRIPTION: SEQ ID NO:9:

Ser Gly Xaa Lys Glu Ile Ile Gln Glu Lys Gln Asn Lys His
 1           5                  10

(2) INFORMATION FOR SEQ ID NO:10:

(i) SEQUENCE CHARACTERISTICS:
    (A) LENGTH: 8 amino acids (B) TYPE: amino acid
        (D) TOPOLOGY: unknown (ii) MOLECULE TYPE: peptide (ix) FEATURE:
        (A) NAME/KEY: Region
        (B) LOCATION: 8
        (D) OTHER INFORMATION: /note="Where X is Cys or Ser."

(xi) SEQUENCE DESCRIPTION: SEQ ID NO:10:

Gln Glu Lys Gln Asn Lys His Xaa
    1               5

(2) INFORMATION FOR SEQ ID NO:11:

(i) SEQUENCE CHARACTERISTICS:
        (A) LENGTH: 26 amino acids
        (B) TYPE: amino acid
        (D) TOPOLOGY: unknown (ii) MOLECULE TYPE: peptide (xi) SEQUENCE DESCRIPTION: SEQ ID NO:11:

Cys Ile Arg Ser Trp Asn Leu Met Lys Gln Gly Ala Ser Ile Lys Glu
    1               5                   10                  15

Ile Ile Gln Glu Lys Gln Asn Lys His Cys
                    20                  25

(2) INFORMATION FOR SEQ ID NO:12:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:12:

Ser Gly Ile Lys Lys Ile Ile Gln Glu Lys Gln Asn Lys Cys
    1               5                       10

(2) INFORMATION FOR SEQ ID NO:13:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (xi) SEQUENCE DESCRIPTION: SEQ ID NO:13:

Ser Gly Ile Lys Glu Ile Ile Gln Lys Lys Gln Asn Lys Cys
    1               5                       10

PROTEIN S POLYPEPTIDES AND ANTI-PEPTIDE ANTIBODIES THAT INHIBIT PROTEIN S BINDING TO C4B BINDING PROTEIN, DIAGNOSTIC SYSTEMS AND THERAPEUTIC METHODS

This invention was made with the support of the United States Government, and the United States Government has certain rights in the invention pursuant to National Institutes of Health Grant HL-21544.

CROSS-REFERENCE TO RELATED APPLICATION

The present application is a continuation-in-part of copending application Ser. No. 07/724,746, abandoned, filed Jul. 2, 1991, the application of which is hereby incorporated by reference.

TECHNICAL FIELD

The present invention relates to polypeptides and anti-peptide antibodies useful for therapeutic methods and compositions for inhibiting protein S binding to C4b binding protein. In addition, the polypeptides and antibodies are useful in diagnostic methods for detecting free protein S in fluid samples.

BACKGROUND

Vitamin K-dependent protein S (PS) is a single chain glycoprotein of 75,000 daltons molecular mass. It serves as a cofactor to activated protein C in the inactivation of factors Va and VIIIa. The concentration of PS in human plasma is approximately 25 mg/l. Protein S is found in citrated plasma at least in two forms, free PS ($PS_F$), comprising about 40% of total PS, and bound to C4b binding protein (C4BP), comprising about 60% of total PS. C4BP is a regulatory protein of the classical pathway of the complement system. Only the free form of PS supports the cofactor activity for activated protein C. Protein S forms complexes with C4BP in the presence of Ca++ and EDTA, and the dissociation constant (Kd) for the interaction is much lower in the presence of Ca++ ($6 \times 10^{-10}$M) than in the presence of EDTA ($10^{-9}$M). This low binding constant suggests that protein S circulating in blood is either completely bound to C4BP or another component that changes the equilibrium between protein S and C4BP might be involved. This third component called protein S binding protein (PSBP) was described in plasma bovine but is not found in human plasma.

The physiological relevance of protein S is demonstrated by the observed increased risk of venous thromboembolism among individuals with congenital protein S deficiency. In addition, 30% of patients exhibiting arterial thrombosis exhibit decreases in plasma PS levels. Therefore, assays for measuring the plasma levels of PS, and particularly the levels of free PS are an important tool for the clinician. The complexation of PS with C4BP removes the anticoagulation active form of PS ($PS_F$) from the circulation.

Previous assays for measuring plasma levels of PS included the use of a pooled normal plasma as a reference standard that contained total PS comprising free ($PS_F$) and complexed (PS:C4BP) PS. Thus the assay must separate free PS from complexed PS in order to identify the amount of $PS_F$ available in the blood. Edson et al., *Am. J. Clin. Path.*, 94:176-186 (1990), reviews laboratory diagnostic methods for detecting free protein S, including the standard two dimensional rocket crossed immunoelectrophoresis (CIEP) procedure of Laurell et al., *Anal. Biochem.*, 10:358-361 (1985), and the two step precipitation procedure of Comp et al., *Blood*, 67:504-508 (1986), using polyethylene glycol to selectively remove PS:C4BP complex from free PS prior to measurement of PS.

Antibodies immunospecific for free PS have not been described. Attempts to develop antibodies that bind the region of PS involved in binding C4BP, and that therefore would inhibit the binding of PS to C4BP have also not been successful. Dahlback et al., *J. Biol. Chem.*, 265:8127-8135 (1990). Thus there is presently no direct means to immunologically distinguish free PS from PS:C4BP complex. Because direct assay of free PS is not presently available, assays for free PS require a separation step to distinguish the immunologically indistinguishable species of free PS from PS:C4BP complex.

Malm et al., describes a monoclonal antibody that immunoreacts with protein S (*Eur. J. Biochem.*, 165:39-45, 1987). The antibody described binds free protein S and binds protein S complexed with C4b binding protein (C4BP), but does not bind thrombin-cleaved protein S, and is therefore proposed to bind an epitope located near the gla domain of protein S.

Recently the synthetic peptide GVQLDLDEAI (SEQ ID NO 6: 3-17) was described that is derived from the carboxy terminal region of protein S (residues 605 to 614 of mature PS) and that inhibits the interaction of protein S with C4BP in vitro. Walker et al., *J. Biol. Chem.*, 264:17645-17648 (1989); and Weinstein et al., *J. Clin Invest.*, 86:1928-1935 (1990). These reports suggest that this region of protein S is important for the binding to C4BP. Other protein S polypeptides corresponding to residues 608-616 and 616-624 were shown to have a measurable effect on the binding of PS to C4BP.

Additional fragments of protein S have been described in the literature that are produced by proteolytic cleavage. Dahlback et al., *J. Biol. Chem.*, 261:5111-5115 (1986); and Stenflo et al., *Natl. Acad. Sci. U.S.A.*, 84:368-372 (1987). However, none of these fragments have been identified as having the capacity to inhibit protein S binding to C4BP.

BRIEF SUMMARY OF THE INVENTION

Regions of protein S have now been discovered that define the site of binding between protein S (PS) and C4b binding protein (C4BP), and are useful to produce PS polypeptides and anti-peptide antibodies that inhibit the binding interaction between PS and C4BP. Additionally, the PS polypeptides and antibodies provide useful diagnostic reagents for measuring free PS in body samples.

Thus, the present invention describes a PS polypeptide having an amino acid residue sequence that corresponds to the sequence of a portion of the mature protein S amino acid residue sequence, and that inhibits protein S binding to C4BP.

Also contemplated are antibody and monoclonal antibody molecules that immunoreact with a PS polypeptide of the present invention and with native PS protein. Preferred antibodies inhibit protein S binding to C4BP.

The invention also describes diagnostic systems and methods in a variety of direct or competitive immunoassay formats for detecting the presence of free protein S in a vascular fluid by the use of the PS polypeptides and antibody molecules of this invention. The assays are based on the specific binding interaction described herein between a PS polypeptide or an antibody with free protein S.

Further contemplated are therapeutic compositions and methods for inhibiting protein S binding to C4BP using the PS polypeptides and antibodies of the invention.

Another embodiment describes the use of the antibodies for purifying free protein S from fluid samples, particularly the use of immobilized antibody molecules.

Other embodiments will be apparent to one skilled in the art.

BRIEF DESCRIPTION OF THE DRAWINGS

FIG. 6, in two figures A and B, illustrates the results of the 2-D electrophoresis described in the assay for free protein S by adsorption using MAb 56 as described in Example 6B.

DETAILED DESCRIPTION OF THE INVENTION

A. Definitions

Figure 1:
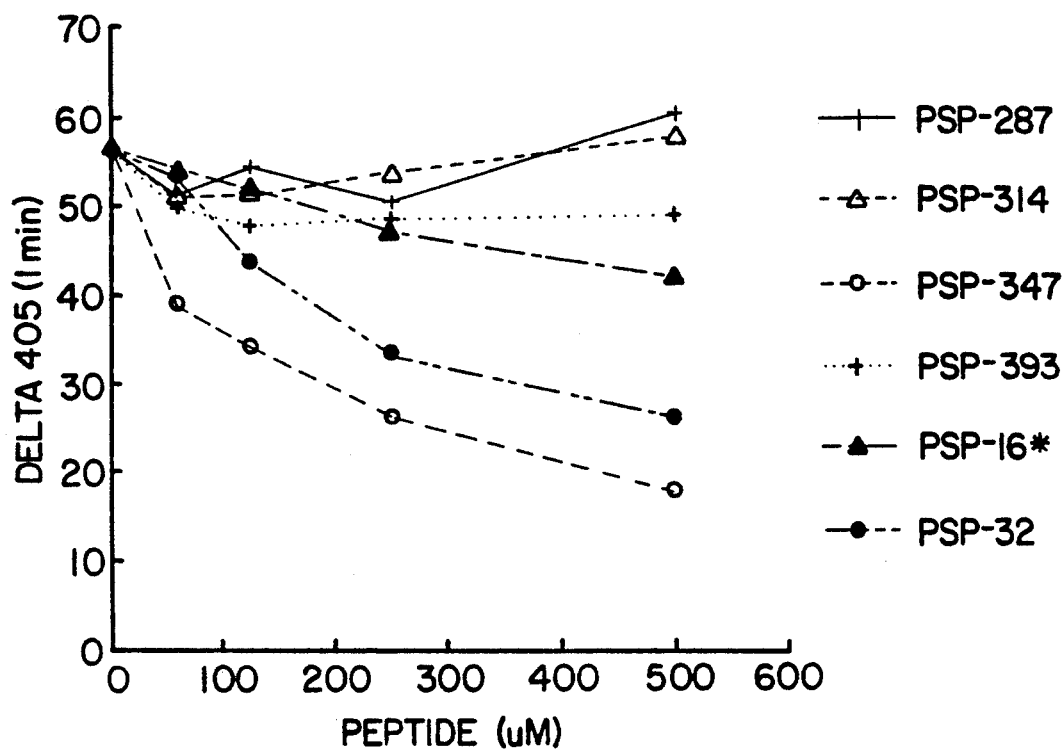
FIG. 1 illustrates the results of the Peptide Inhibition Assay described in Example 5Aii. Varying concentrations of the peptides listed were incubated with the protein C4BP which was coated to microtiter wells of a 96 well plate. Subsequently biotinylated protein S (b-PS) was added to the wells and the amount of b-PS which bound to C4BP was detected as described in Example 2C. Other peptides shown in FIGS. 1-3 but not listed in Table 1 include: PSP-287 (1:287-301); PSP-314 (1:314-328); PSP-393 (1:393-407); PSP-48 (1:48-62); PSP-57 (1:57-71); PSP-172 (1:172-186); PSP-19 (1:621-635); and (PSP-425A (1:425-433). The SEQ ID NO and corresponding amino acid residue positions are indicated in the parentheses.
Figure 2:
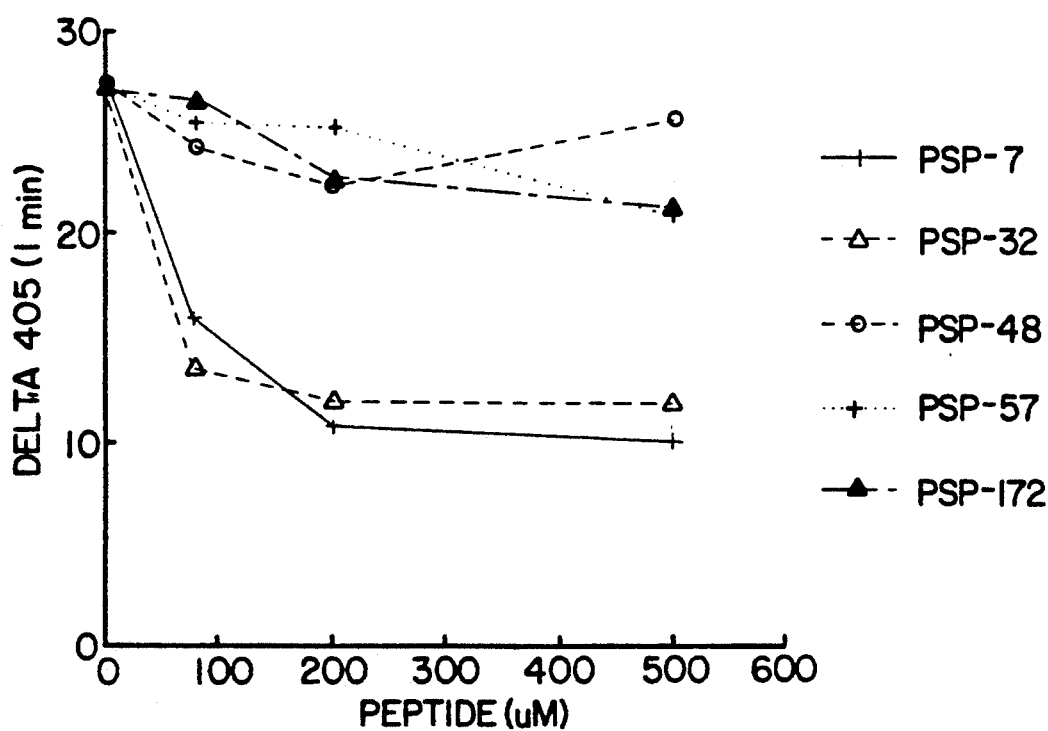
FIGS. 2, 3 and 4 also illustrate the results of the Peptide Inhibition Assay described in Example 5Aii and in the legend to FIG. 1.
Figure 3:
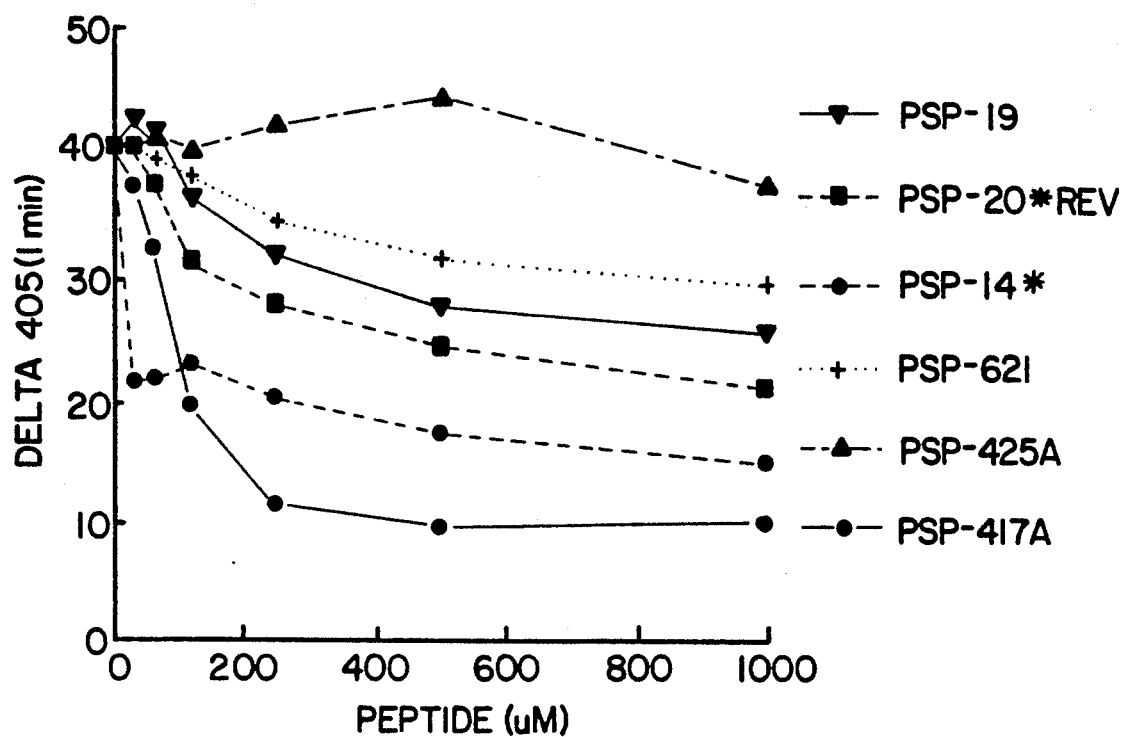
Figure 4:
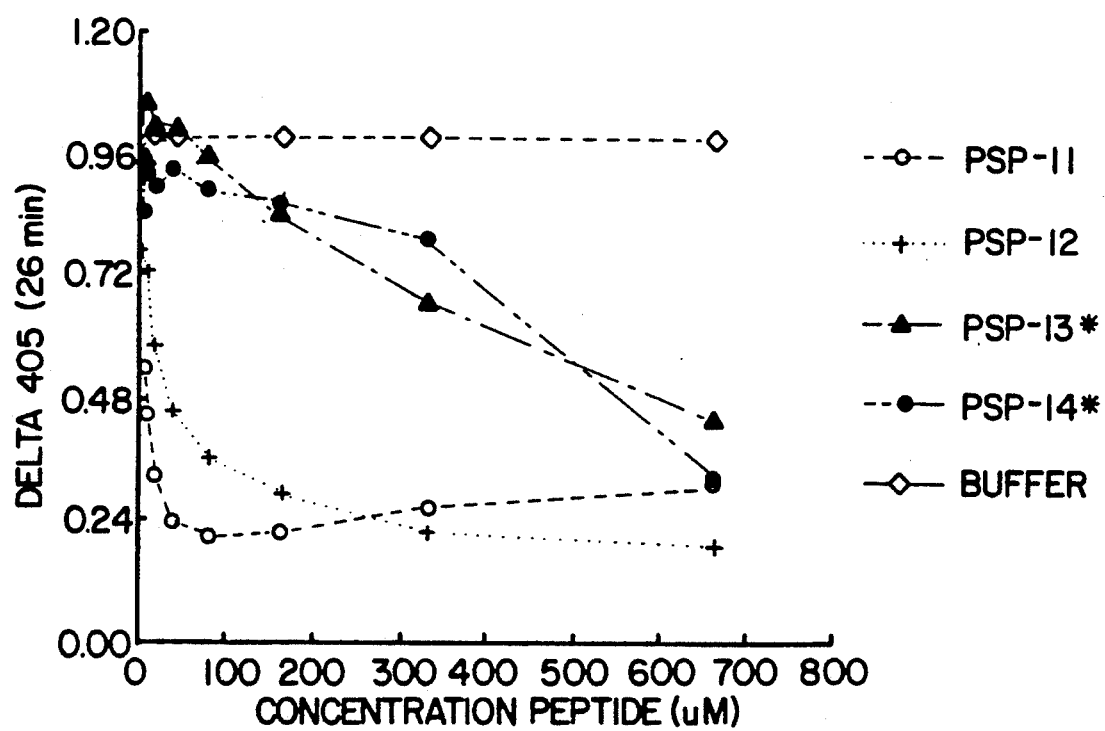

Amino Acid Residue: An amino acid formed upon chemical digestion (hydrolysis) of a polypeptide at its peptide linkages. The amino acid residues identified herein are preferably in the natural "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3553-59 (1969) and adopted at 37 CFR §1.822(b)(2), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |
| X | Xaa | any amino acid |
| B | Asx | aspartic acid or asparagine |
| Z | Glx | glutamic acid or glutamine |

It should be noted that all amino acid residue sequences are represented herein by formulae whose left and right orientation is in the conventional direction of amino-terminus to carboxy-terminus. In addition, the phrase "amino acid residue" is broadly defined to include modified and unusual amino acids, such as those listed in 37 CFR §1.822(b)(4), and are incorporated by reference. Furthermore, it should be noted that a dash at the beginning or end of an amino acid residue sequence indicates either a peptide bond to a further sequence of one or more amino acid residues or a covalent bond to a carboxyl or hydroxyl end group.

Activated Protein C: Activated Protein C refers to Protein C that is cleaved proteolytically by thrombin to yield an activated protein C (APC) which inactivates coagulation Factors Va and VIIIa thus inhibiting coagulation.

Antibody: The term antibody in its various grammatical form is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')2 and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Factor V: Factor V is a high molecular weight protein that, when activated by thrombin, can accelerate the conversion of prothrombin to thrombin by Factor Xa which promotes coagulation. Activated factor Va is inactivated by activated Protein C to inhibit the coagulation process.

Factor VIII: Factor VIII, is called the antihemophilic factor in blood coagulation, is a high molecular weight protein involved in the activation of Factor X in concert with Factor Xa. Activated Factor VIIIa is inactivated by activated Protein C to inhibit the coagulation process.

Factor X: Factor X is a zymogen of a serine protease which has a molecular weight of 55,000. When activated, Factor Xa in concert with Factor Va causes the conversion of prothrombin to thrombin which promotes coagulation.

Monoclonal Antibody: The phrase monoclonal antibody in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

Polypeptide and Peptide: Polypeptide and peptide are terms used interchangeably herein to designate a linear series of amino acid residues connected one to the other by peptide bonds between the alpha-amino and carboxy groups of adjacent residues.

Protein C: Protein C (PC) is a vitamin K-dependent serine protease zymogen and shares sequence homology with other known vitamin K-dependent serine proteases. In the presence of endothelial cell thrombomodulin and thrombin, Protein C is activated to a serine protease, APC, and becomes a potent inhibitor of blood coagulation by inactivating Factor Va and Factor VIIIa.

Protein S: Protein S (PS) is a vitamin k-dependent plasma protein which serves as a co-factor to activated Protein C in the inactivation of Factors Va and VIIIa.

Serine Proteases: Serine proteases are a family of protein-cleaving (proteolytic) enzymes of which activated Protein C is a member.

Synthetic Peptide: Synthetic peptide refers to a chemically produced chain of amino acid residues linked together by peptide bonds that is free of naturally occurring proteins and fragments thereof.

B. Polypeptides

As used herein, the phrase "PS polypeptide" refers to a polypeptide having an amino acid residue sequence that comprises an amino acid residue sequence that corresponds, and preferably is identical, to a portion of the protein S molecule. The amino acid residue sequence of the mature protein S protein is listed as SEQ ID NO 1 in the sequence listing. Preferably, a PS polypeptide of the present invention has the capacity to inhibit the binding of protein S (PS) to C4b binding protein (C4BP).

A PS polypeptide is preferably no more than about 200 amino acid residues in length for reasons of ease of synthesis and ability to direct the inhibition to a precise contact site on the PS:C4BP complex. Thus, it is more preferred that a PS polypeptide be no more that about 100 amino acid residues, still more preferably no more than about 50 residues, and most preferably less than 20 amino acid residues in length.

In one embodiment, a PS polypeptide of the present invention has a length of no more than about 100 amino acid residues, and includes an amino acid residue sequence represented by the formula: -KEIIQ-, said sequence shown in SEQ ID NO 1 from residue 423 to residue 427.

The SEQ ID NO and corresponding residues of a described amino acid residue sequence are conveniently described herein in parenthesis, where the first number is the SEQ ID NO and the range following the colon represents the residue numbers of the indicated amino acid residues in the Sequence Listing. For example, "(1:423–427)" refers to the sequence KEIIQ shown in SEQ ID NO 1 from residue 423 to residue 427. For the peptides listed in the Sequence Listing with SEQ ID NOs 2–13, the range following the colon also represents the residue numbers of the indicated amino acid residues. For SEQ ID NOs 2–13, the corresponding residue positions of these peptides derived from the protein S sequence in SEQ ID NO 1 are indicated by the range after the forward slash, e.g., SGVKEIIQEKQNKHS (3:1–15/420–434). These corresponding positions are only indicated in Table 1 below for SEQ ID NOs 2–8 and 11–13. The positions are indicated in the text for SEQ ID NOs 9 and 10.

In this embodiment, a preferred PS polypeptide includes an amino acid residue sequence represented by the formula -KEIIQEKQNKH- (1:423–433), and more preferably includes an amino acid residue sequence represented by the formula -SGXKEIIQEKQNKH- (9:1–14/420–433), where X is I or V, preferably I. An exemplary and preferred polypeptide in this embodiment has an amino acid residue sequence selected from the group consisting of:

| | |
|---|---|
| SGIKEIIQEKQNKHC, | (1:420–434) |
| SGIKEIIQEKQNKHS, | (2:1–15) |
| SGVKEIIQEKQNKHS, | (3:1–15) |
| KEIIQEKQNKHS, | (2:4–15) |
| GASGIKEIIQEKQNK, | (1:418–432) |
| NLMKQGASGIKEIIQ, | (1:413–427) |
| GIKEIIQ, and | (1:421–427) |
| CIRSWNLMKQGAS IKEIIQEKQNKHC | (11:1–26) |

Particularly preferred is the PS polypeptide shown in SEQ ID NO 1 from residue 420 to residue 434.

Another particularly preferred PS polypeptide of the present invention is shown in SEQ ID NO 11 that has an amino acid residue sequence represented by the formula CIRSWNLMKQGASIKEIIQEKQNKHC (11:1–26). This PS peptide was synthesized without the glycine (G) residue normally present in the native PS protein at amino acid residue position 421 which corresponds to the amino acid residue position between 13 and 14 in SEQ ID NO 11. This PS peptide is also referred to as the loop peptide.

In a related embodiment, a PS polypeptide is contemplated as having a length no more than about 100 amino acid residues that includes an amino acid residue sequence represented by the formula: -SGIKKIIQEKQNKC- (12:1-14). In this embodiment, an exemplary and preferred polypeptide has an amino acid residue sequence represented by the formula SGIKKIIQEKQNKC (12:1-14). This PS peptide was synthesized without the histidine (H) residue normally present in the native PS protein at amino acid residue position 433 which corresponds to the amino acid residue position between 13 and 14 in SEQ ID NO 12.

In another related embodiment, a PS polypeptide is contemplated as having a length no more than about 100 amino acid residues that includes an amino acid residue sequence represented by the formula: -SGIKEIIQKKQNKC- (13:1-14). In this embodiment, an exemplary and preferred polypeptide has an amino acid residue sequence represented by the formula SGIKEIIQKKQNKC (13:1-4). This PS peptide was synthesized without the histidine (H) residue normally present in the native PS protein at amino acid residue position 433 which corresponds to the amino acid residue position between 13 and 14 in SEQ ID NO 13.

In an additional embodiment, a PS polypeptide of the present invention has a length of no more than about 100 amino acid residues, and includes an amino acid residue sequence represented by the formula: -SGIKE- (1:420-424). In this embodiment, an exemplary and preferred polypeptide has an amino acid residue sequence selected from the group consisting of:

| GASGIKEIIQEKQNK, | (1:418-432) |
| NLMKQGASGIKEIIQ, and | (1:413-427) |
| QGASGIKE. | (1:417-424) |

Further embodiments contemplate a PS polypeptide of the present invention having a length of no more than about 100 amino acid residues that includes an amino acid residue sequence represented by the formula: -QEKQNKHX- (10:-8/427-434) where X is C or S. In this embodiment, an exemplary and preferred polypeptide has the amino acid residue sequence represented by the formula QEKQNKHS (2:8-15).

In another embodiment, a PS polypeptide of the present invention has a length of no more than about 100 amino acid residues, and includes an amino acid residue sequence represented by the formula: -QGASGI- (1:417-422), and more preferably includes an amino acid residue sequence represented by the formula -QGASGIKE- (1:417-4-24). In this embodiment, an exemplary and preferred polypeptide has an amino acid residue sequence selected from the group consisting of:

| QGASGIKE, | (1:417-424) |
| NLMKQGASGIKE, and | (1:413-424) |
| NLMKQGASGI. | (1:413-422) |

Another related embodiment contemplates a PS polypeptide having a length of no more than about 100 amino acid residues that includes an amino acid residue sequence represented by the formula: -NLMKQG- (1:413-418), and more preferably includes an amino acid residue sequence represented by the formula -NLMKQGASGI- (1:413-422). In this embodiment, an exemplary and preferred polypeptide has an amino acid residue sequence selected from the group consisting of:

| NLMKQGASGIKE | (1:413-424) |
| NLMKQGASGI | (1:413-422) |
| CIRSWNLMKQGASGI | (1:408-422) |
| DIRSWNLMKQGASGI | (4:408-422) |
| DIRSWNLMKQG | (4:408-418) |

In another embodiment, a PS polypeptide of the present invention has a length of no more than about 100 amino acid residues, and includes an amino acid residue sequence represented by the formula: -ENDPETDYFYPKYLV- (1:32-46). In this embodiment, an exemplary and preferred polypeptide has an amino acid residue sequence represented by the formula ENDPETDYFYPKYLV (1:32-46).

Another embodiment contemplates a PS polypeptide having a length of no more than about 100 amino acid residues that includes an amino acid residue sequence represented by the formula: -PEGYRYNLKSKS- (1:188-199). In this embodiment, an exemplary and preferred polypeptide has an amino acid residue sequence represented by the formula selected from the group consisting of:

| CPEGYRYNLKSKSC, and | (1:187-200) |
| SPEGYRYNLKSKSSE. | (5:1-15) |

In another embodiment, a PS polypeptide of the present invention has a length of no more than about 100 amino acid residues, and includes an amino acid residue sequence represented by the formula: -VEELEHSISIKIAKE- (1:347-361). In this embodiment, an exemplary and preferred polypeptide has an amino acid residue sequence represented by the formula VEELEHSISIKIAKE (1:347-361).

Another embodiment contemplates a PS polypeptide having a length of no more than about 100 amino acid residues, and includes an amino acid residue sequence represented by the formula: -INGVQLDLDEAISK- (1:603-616). In this embodiment, an exemplary and preferred polypeptide has an amino acid residue sequence represented by the formula INGVQLDLDEAISKC (6:1-15).

In another embodiment, a PS polypeptide of the present invention has a length of no more than about 100 amino acid residues, and includes an amino acid residue sequence represented by the formula: -RAHSCPS- (1:621-627), and more preferably includes an amino acid residue sequence represented by the formula -RAHSCPSVWKKTKN- (1:621-634). In this embodiment, an exemplary and preferred polypeptide has an amino acid residue sequence selected from the group consisting of:

| RAHSCPS, and | (1:621-627) |
| RAHSCPSVWKKTKNC. | (7:1-15) |

In view of the relatedness of the various before-described PS polypeptides, due to their capacity to inhibit PS:C4BP complex formation, the present invention also contemplates a PS polypeptide having a length of no more than about 100 amino acid residues and including an amino acid residue sequence represented by a formula selected from the group consisting of:

| | |
|---|---|
| -ENDPETDYFYPKYLV-, | (1:32–46) |
| -PEGYRYNLKSKS-, | (1:188–199) |
| -VEELEHSISIKIAKE-, | (1:347–361) |
| -NLMKQG-, | (1:413–418) |
| -QGASGI-, | (1:417–422) |
| -KEIIQ-, | (1:423–427) |
| -QEKQNKHX-, | (10:1–8/427–433) |
| -INGVQLDLDEAISK-, | (1:603–616) |
| -RAHSCPS-, | (1:621–627) |
| -SGIKKIIQEK-, and | (12:1–14) |
| -SGIKEIIQKK- | (13:1–14) | wherein X is C or S, and wherein said polypeptide inhibits binding of protein S to C4b binding protein, thereby inhibiting formation of a PS:C4BP complex. A particularly preferred PS polypeptide for inhibiting PS:C4BP complex formation has an amino acid residue sequence represented by a formula selected from the group consisting of:

| | |
|---|---|
| ENDPETDYFYPKYLV, | (1:32–46) |
| CPEGYRYNLKSKSC, | (1:187–200) |
| SPEGYRYNLKSKSSE, | (5:1–15) |
| VEELEHSISIKIAKE | (1:347–361) |
| QGASGIKE, | (1:417–424) |
| NLMKQGASGIKE, | (1:413–424) |
| NLMKQGASGI, | (1:413–422) |
| CIRSWNLMKQGASGI, | (1:408–422) |
| DIRSWNLMKQGASGI, | (4:1–15) |
| DIRSWNLMKQG, | (4:1–11) |
| CIRSWNLMKQGASIKEIIQEKQNKHC | (11:1–26) |
| SGIKEIIQEKQNKHC, | (1:420–434) |
| SGIKEIIQEKQNKHS, | (2:420–434) |
| SGVKEIIQEKQNKHS, | (3:420–434) |
| SGIKKIIQEKQNKC | (12:1–14) |
| SGIKEIIQKKQNKC | (13:1–14) |
| KEIIQEKQNKHS, | (2:423–434) |
| GASGIKEIIQEKQNK, | (1:418–432) |
| NLMKQGASGIKEIIQ, | (1:413–427) |
| GIKEIIQ, | (1:421–427) |
| GASGIKEIIQEKQNK, | (1:418–432) |
| NLMKQGASGIKEIIQ, | (1:413–427) |
| QEKQNKHS, | (2:427–434) |
| INGVQLDLDEAISKC, | (6:1–15) |
| RAHSCPS, and | (1:621–627) |
| RAHSCPSVWKKTKNC. | (7:1–15) |

Preferred PS polypeptides, their designations, and their PS amino acid residue positions are shown in Table 1.

TABLE 1

| Polypeptide Designation | Amino Acid Residue Sequence[1] | SEQ ID NO |
|---|---|---|
| PSP-12 | SGIKEIIQEKQNKHC | (1:420–434) |
| PSP-12* | SGIKEIIQEKQNKH<u>S</u> | (2:1–15/420–434) |
| PSP-12b* | SGVKEIIQEKQNKH<u>S</u> | (3:1–15/420–434) |
| PSP-428* | KEIIQEKQNKH<u>S</u> | (2:4–15/423–434) |
| PSP-430* | QEKQNKH<u>S</u> | (2:8–15/427–434) |
| PSP-425 | GASGIKEIIQEKQNK | (1:418–432) |
| PSP-420 | NLMKQGASGIKEIIQ | (1:413–427) |
| PSP-424 | GIKEIIQ | (1:421–427) |
| PSP-417A | QGASGIKE | (1:417–424) |
| PSP-417 | NLMKQGASGI | (1:413–422) |
| PSP-417B | NLMKQGASGIKE | (1:413–424) |
| PSP-11 | CIRSWNLMKQGASGI | (1:408–422) |
| PSP-418* | <u>D</u>IRSWNLMKQGASGI | (4:1–15/408–422) |
| PSP-415* | <u>I</u>RSWNLMKQG | (4:408–418) |
| PSP-347 | VEELEHSISIKIAKE | (1:347–361) |
| PSP-32 | ENDPETDYFYPKYLV | (1:32–46) |
| PSP-7 | CPEGYRYNLKSKSC | (1:187–200) |
| PSP-16* | <u>S</u>PEGYRYNLKSKS<u>SE</u> | (5:1–15/187–201) |
| PSP-13* | INGVQLDLDEAISK<u>C</u> | (6:1–15/603–616) |
| PSP-14* | RAHSCPSVWKKTKN<u>C</u> | (7:1–15/621–635) |
| PSP-621 | RAHSCPS | (1:621–627) |
| PSP-20*REV | SNKTKKWVSP<u>SS</u>HAR | (8:1–15/635–621) |
| PSP-54 | GLFTAARQSTNAYP | (1:54–67) |
| PSP-561 | RQLAVLDKAMKAKV | (1:561–574) |
| PSP-605 | GVQLDLDEAI | (1:605–614) |
| PSP-loop | CIRSWNLMKQGASIKEIIQEKQNKHC | (11:1–26/408–420,422–434) |
| PSP-424K* | SQIK<u>K</u>IIQEKQNKC | (12:1–14/420–432,434) |
| PSP-428K* | SGIKEIIQ<u>K</u>KQNKC | (13:1–14/420–432,434) |

[1]An underlined amino acid residue and the asterisk by the polypeptide designation both indicate a substitution relative to the amino acid residue sequence of native PS. The amino acid residue sequence of the polypeptide is shown, together with parenthesis indicating the SEQ ID NO and amino acid residue number designation. For amino acid sequences labeled as SEQ ID NO 1, the residue number column indicates the position numbers of the peptide sequence. For peptides with SEQ ID NOs 2–8, 11–13, the first range behind the colon indicates the amino acid residue number designation as it appears in the Sequence Listing. The second range following the forward slash indicates the amino residue position corresponding to the relative positions in the native PS sequence in SEQ ID NO 1.

Due to the three dimensional structure of a native folded protein S molecule, it has been determined in the present invention that multiple regions of protein S are involved in contacting C4BP when a PS:C4BP complex is formed, which multiple and various regions are defined by the various PS polypeptides described above. The ability of the above-described PS polypeptides to inhibit PS binding to C4BP is shown in the Examples herein.

Thus, in another embodiment, the invention contemplates PS polypeptide compositions that comprise one or more of the different PS polypeptides described above, admixed in combinations to provide simultaneous inhibition of multiple contact sites formed in a PS:C4BP complex.

Preferably, a PS polypeptide of this invention is further characterized by its ability to immunologically mimic an epitope (antigenic determinant) expressed by PS. Such a polypeptide is useful herein as a component in an inoculum for producing antibodies that immunoreact with native PS protein, and preferably immunoreact with free PS.

As used herein, the phrase "immunologically mimic" in its various grammatical forms refers to the ability of an PS polypeptide of this invention to immunoreact with an antibody of the present invention that recognizes a conserved native epitope of PS as defined herein.

It should be understood that a subject polypeptide need not be identical to the amino acid residue sequence of PS, so long as it includes the required sequence and is able to inhibit PS binding to C4BP as described herein.

A subject polypeptide includes any analog, fragment or chemical derivative of a polypeptide whose amino acid residue sequence is shown herein so long as the polypeptide is capable of inhibiting protein S binding to C4BP. Therefore, a present polypeptide can be subject to various changes, substitutions, insertions, and deletions where such changes provide for certain advantages in its use. In this regard, a PS polypeptide of this invention corresponds to, rather than is identical to, the sequence of protein S where one or more changes are made and it retains the ability to inhibit protein S binding to C4BP in one or more of the assays as defined herein for determining inhibition of PS:C4BP complex formation.

The term "analog" includes any polypeptide having an amino acid residue sequence substantially identical to a sequence specifically shown herein in which one or more residues have been conservatively substituted with a functionally similar residue and which displays the ability to PS:C4BP complex formation as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Exemplary substitutions can be seen in several of the inhibitory PS polypeptides described herein having sequences that are not identical to the sequence of native PS.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of PS, it is typically because one or more conservative or non-conservative substitutions have been made, usually no more than about 30 number percent, more usually no more than 20 number percent, and preferably no more than 10 number percent of the amino acid residues are substituted. Additional residues may also be added at either terminus for the purpose of providing a "linker" by which the polypeptides of this invention can be conveniently affixed to a label or solid matrix, or carrier. Preferably the linker residues do not form PS epitopes, i.e., are not similar is structure to the PS.

Labels, solid matrices and carriers that can be used with the polypeptides of this invention are described hereinbelow.

Amino acid residue linkers are usually at least one residue and can be 40 or more residues, more often 1 to 10 residues, but do not form PS epitopes. Typical amino acid residues used for linking are tyrosine, cysteine, lysine, glutamic and aspartic acid, or the like. In addition, a subject polypeptide can differ, unless otherwise specified, from the natural sequence of PS by the sequence being modified by terminal-NH$_2$ acylation, e.g., acetylation, or thioglycolic acid amidation, by terminal-carboxylamidaton e.g., with ammonia, methylamine, and the like.

When coupled to a carrier to form what is known in the art as a carrier-hapten conjugate, a PS polypeptide of the present invention is capable of inducing antibodies that immunoreact with PS. In view of the well established principle of immunologic cross-reactivity, the present invention therefore contemplates antigenically related variants of the polypeptides shown in Table 1. An "antigenically related variant" is a subject polypeptide that is capable of inducing antibody molecules that immunoreact with a polypeptide from Table 1 and with PS.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

A PS polypeptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

A PS polypeptide can be used, inter alia, in the diagnostic methods and systems of the present invention to detect PS present in a body sample, or can be used to prepare an inoculum as described herein for the preparation of antibodies that immunoreact with conserved epitopes on PS.

In addition, a PS polypeptide of this invention can be used in the therapeutic methods of the present invention to inhibit protein S binding to C4b binding protein and thereby inhibit thrombosis and anticoagulation.

C. Antibodies and Monoclonal Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

An antibody of the present invention, i.e., an anti-PS antibody, in one embodiment is characterized as comprising antibody molecules that immunoreact with: 1) isolated protein S, and 2) a PS polypeptide of the present invention, and being substantially free of antibody molecules that immunoreact with 1) protein S when present in a complex with C4b binding protein (C4BP), the complex being referred to herein as PS:C4BP complex, and 2) the polypeptide: CTCKPGWQGEKCEF-DINECKDPSNINGGCS, (1:103-131).

By "substantially free" means that the antibody molecules do not immunoreact with the stated antigen at levels within one order of magnitude, and preferably within two orders of magnitude, of the level of immunoreaction with a species of antigen recited to immunoreact with the antibody molecule when immunoreaction is expressed as an equilibrium constant between bound (immunoreacted) and nonbound antigen.

Based on the teachings herein, it has been discovered that antibody molecules that immunoreact with a PS polypeptide of the present invention have the capacity to immunoreact with a site on PS that is not accessible to immunoreaction when PS is complexed with C4BP. Thus, the antibody molecules of this invention do not immunoreact with PS:C4BP complex but do bind $PS_F$.

An anti-PS antibody that immunoreacts with PS but does not immunoreact with PS in a PS:C4BP complex is referred to herein as immunoreacting with "free PS", also referred to herein as $PS_F$. Such an antibody is also referred to herein as an anti-$PS_F$ antibody, an antibody that immunoreacts with $PS_F$, and as an antibody that is immunospecific for $PS_F$, i.e., does not bind PS:C4BP complex. Such an antibody is particularly useful, as described further herein, for use in diagnostic assays to measure $PS_F$ in a fluid sample.

In addition, a preferred anti-PS antibody immunospecific for PS$_F$ has the capacity to inhibit protein S binding to C4b binding protein.

In preferred embodiments, an anti-PS antibody is characterized as being capable of immunoreacting with a polypeptide having an amino acid residue sequence represented by the formula selected from the group consisting of:

| | |
|---|---|
| SGIKEIIQEKQNKHC, | (1:420-434) |
| SGIKKIIQEKQNKC | (12:1-14) |
| SGIKEIIQKKQNKC | (13:1-14) |
| GASGIKEIIQEKQNK, | (1:418-432) |
| NLMKQGASGIKEIIQ, | (1:413-427) |
| CIRSWNLMKQGASGI, | (1:408-422) |
| CIRSWNLMKQGASIKEIIQEKQNKHC | (11:1-26) |
| VEELEHSISIKIAKE, | (1:437-361) |
| ENDPETDYFYPKYLV, | (1:32-46) |
| CPEGYRYNLKSKSC, | (1:187-200) |
| SPEGYRYNLKSKSSE, | (5:1-15) |
| INGVQLDLDEAISKC, and | (6:1-15) |
| RAHSCPSVWKKTKNC.. | (7:1-15) |

Particularly preferred anti-PS antibodies immunoreact with a PS polypeptide having a sequence that includes the epitope defined by the formula: -KEIIQ- (1:423-427). More preferred are anti-PS antibodies that immunoreact with the polypeptide according to the formula SGIKEIIQEKQNKHC (1:420-434).

Most preferred are anti-PS antibodies that immunoreact with the loop polypeptide according to the formula CIRSWNLMKQGASIKEIIQEKQNKHC (11:1-26).

Antibody immunoreactivity with PS-containing antigens can be measured by a variety of immunological assays known in the art. Exemplary immunoreaction of an anti-PS antibody with a PS polypeptide is described in Example 2. Direct binding with isolated PS (prepared as described in Example 2c), and with PS polypeptides can be assayed at least by the methods described in Example 2.

An antibody of the present invention is typically produced by immunizing a mammal with an inoculum containing an PS polypeptide of this invention and thereby induce in the mammal antibody molecules having immunospecificity for immunized PS polypeptide. The antibody molecules are then collected from the mammal and isolated to the extent desired by well known techniques such as, for example, by using DEAE Sephadex to obtain the IgG fraction. Exemplary antibody preparation methods using PS polypeptides in the immunogen are described herein at Example 2.

The preparation of antibodies against polypeptide is well known in the art. [See Staudt et al., J. Exp. Med., 157:687-704 (1983)]. Briefly, to produce a peptide antibody composition of this invention, a laboratory mammal is inoculated with an immunologically effective amount of a PS polypeptide, typically as present in a vaccine of the present invention. The anti-PS polypeptide antibody molecules thereby induced are then collected from the mammal and those immunospecific for both the PS polypeptide and isolated PS are isolated to the extent desired by well known techniques such as, for example, by immunoaffinity chromatography.

To enhance the specificity of the antibody, the antibodies are preferably purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques. Exemplary immunoaffinity purification methods for producing an immunoaffinity purified anti-PS antibody of this invention are described in Example 3.

The word "inoculum" in its various grammatical forms is used herein to describe a composition containing a PS polypeptide of this invention as an active ingredient used for the preparation of antibodies against an PS polypeptide. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide" and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used.

The techniques of polypeptide conjugation or coupling through activated functional groups presently known in the art are particularly applicable. See, for example, Aurameas, et al., Scand. J. Immunol., Vol. 8, Suppl. 7:7-23 (1978) and U.S. Pat. Nos. 493,795, 3,791,932 and 3,839,153. In addition, a site-directed coupling reaction can be carried out so that any loss of activity due to polypeptide orientation after coupling can be minimized. See, for example, Rodwell et al., Biotech., 3:889-894 (1985), and U.S. Pat. No. 4,671,958.

Exemplary additional linking procedures include the use of Michael addition reaction products, dialdehydes such as glutaraldehyde, Klipstein, et al., J. Infect. Dis., 147:318-326 (1983) and the like, or the use of carbodiimide technology as in the use of a water-soluble carbodiimide to form amide links to the carrier. Alternatively, the heterobifunctional cross-linker SPDP (N-succinimidyl-3-(2-pyridyldithio) proprionate)) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly D-lysine:D-glutamic acid, and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen is well known in the art. Inocula typically contain polypeptide concentrations of about 10 micrograms (μg) to about 500 milligrams (mg) per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The antibody so produced can be used, inter alia, in the diagnostic methods and systems of the present invention to detect free PS (PS not bound to C4BP) present in a sample such as a body fluid sample. See, for example, the methods described at least in Example 6. Anti-PS antibodies that inhibit protein S binding to C4BP can also be used in vivo in therapeutic methods as an anticoagulant and antithrombotic. Assays for measuring the capacity to inhibit PS binding to C4BP are described in Example 5.

A preferred anti-PS antibody is a monoclonal antibody and is used herein as exemplary of an anti-PS antibody.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A monoclonal antibody of this invention comprises antibody molecules that inhibit protein S binding to C4b binding protein as described herein. A monoclonal antibody of this invention is further characterized as being capable of immunoreacting with 1) isolated protein S, and 2) a PS polypeptide of the present invention as described for the anti-PS antibodies of this invention.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature*, 256:495-497 (1975), the description of which is incorporated by reference. The hybridoma supernates so prepared can be screened for the presence of antibody molecules that immunoreact with a PS polypeptide, or for inhibition of PS binding to C4BP as described further herein.

Briefly, to form the hybridoma from which the monoclonal antibody composition is produced, a myeloma or other self-perpetuating cell line is fused with lymphocytes obtained from the spleen of a mammal hyperimmunized with a PS antigen, such as is present in a PS polypeptide of this invention. The polypeptide-induced hybridoma technology is described by Niman et al., *Proc. Natl. Acad. Sci., U.S.A.*, 80:4949-4953 (1983), the description of Which is incorporated herein by reference.

It is preferred that the myeloma cell line used to prepare a hybridoma be from the same species as the lymphocytes. Typically, a mouse of the strain 129 G1X+ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the enzyme linked immunosorbent assay (ELISA) described in Example 4.

A monoclonal antibody of the present invention can also be produced by initiating a monoclonal hybridoma culture comprising a nutrient medium containing a hybridoma that produces and secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's Minimal Essential Medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci. U.S.A.*, 86:5728-5732 (1989); and Huse et al., *Science*, 246:1275-1281 (1989).

The monoclonal antibodies of this invention can be used in the same manner as disclosed herein for antibodies of the present invention.

For example, the monoclonal antibody can be used in the therapeutic, diagnostic or in vitro methods disclosed herein where inhibition of protein S binding to C4b binding protein is desired.

Also contemplated by this invention is the hybridoma cell, and cultures containing a hybridoma cell that produce a monoclonal antibody of this invention.

A particularly preferred monoclonal antibody is the monoclonal antibody produced by the hybridoma LJS 56 (MAb 56) that immunoreacts with $PS_F$ and the PS polypeptide PSP-12 having the amino acid residue sequence SGIKEIIQEKQNKHC (1:420–434). The hybridoma also immunoreacts with the PS polypeptide referred to as PSP-loop having the amino residue sequence CIRSWNLMKQGASIKEIIQEKQNKHC (11:1–26). MAb 56 was produced as described in Example 4 using PS polypeptide PSP-12 as the immunogen. A second monoclonal antibody, functionally equivalent to MAb 56, was isolated by the same methods and is designated as MAb 418.

Hybridoma LJS 56 has been deposited pursuant to Budapest Treaty requirements with the American Type Culture Collection (ATCC), Rockville, Md., on Jun. 26, 1991, and was assigned accession number HB 10818.

Another monoclonal antibody produced by the hybridoma LJS S-7 (MAb S-7) immunoreacts with PS when present in a PS:C4BP complex and is used herein as a capture antibody that immunoreacts with "total PS", also referred to as $PS_T$. MAb S-7 was produced as described in Example 6 using isolated PS as the immunogen.

Hybridoma LJS S-7 has been deposited pursuant to Budapest Treaty requirements with the American Type Culture Collection (ATCC), Rockville, Md., on June 26, 1991, and was assigned accession number HB 10819.

Hybridomas LJS 56 and LJS S-7 were deposited in a depository affording permanence of the deposit and ready accessibility thereto by the public upon the issuance of a patent, under conditions which assure that access to the hybridomas will be available during the pending of the patent application to those deemed by the Commissioner to be entitled to such access, and that all restrictions on the availability to the public of the hybridomas as deposited will be irrevocably removed upon the granting of the patent. The deposited hybridomas will be maintained by the ATCC for the term of the patent or 30 years from the date of deposit, whichever is longer, and in all events for at least five years after the date of the last request for access.

D. Diagnostic Systems

The present invention also describes a diagnostic system, preferably in kit form, for assaying for the presence of free protein S ($PS_F$) in a fluid sample, such as blood, plasma or serum, where it is desirable to detect the presence, and preferably the amount, of $PS_F$ in a sample according to the diagnostic methods described herein. The diagnostic system includes, in an amount sufficient to perform at least one assay, a subject PS polypeptide and/or a subject antibody or monoclonal antibody of the present invention, as a separately packaged reagent.

Exemplary diagnostic systems for detecting $PS_F$ in a body sample and utilizing a PS polypeptide or antibody of this invention are described in Example 6.

In another embodiment, a diagnostic system, preferably in kit form, is contemplated for assaying for the presence of a PS polypeptide or anti-PS antibody in a body fluid sample such as for monitoring the fate of therapeutically administered PS polypeptide or anti-PS antibody. The system includes, in an amount sufficient for at least one assay, a subject PC polypeptide and/or a subject antibody as a separately packaged immunochemical reagent.

In another embodiment, a diagnostic system, preferably in kit form, is contemplated for assaying according to the methods herein for the presence of C4b binding protein (C4BP) that is able to bind (competent for binding) with PS in a body fluid sample such as blood, plasma or serum. Such a species of C4BP is referred to herein as competent C4BP. In view of the presence of several forms of C4BP in vascular fluids, some of which are not able to bind $PS_F$ because they are already complexed with PS or because they represent species of C4BP incapable of binding PS, detecting the presence, and preferably the amount, of competent C4BP in a vascular fluid is desirable. The system includes, in an amount sufficient for at least one assay, a subject PC polypeptide and/or a subject antibody as a separately packaged immunochemical reagent. Exemplary systems are described in Example 7.

Instructions for use of the packaged reagent(s) are also typically included.

As used herein, the term "package" refers to a solid matrix or material such as glass, plastic (e.g., polyethylene, polypropylene or polycarbonate), paper, foil and the like capable of holding within fixed limits a polypeptide, polyclonal antibody or monoclonal antibody of the present invention. Thus, for example, a package can be a glass vial used to contain milligram quantities of a contemplated polypeptide or antibody or it can be a microtiter plate well to which microgram quantities of a contemplated polypeptide or antibody have been operatively affixed, i.e., linked so as to be capable of being immunologically bound by an antibody or antigen, respectively.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

A diagnostic system of the present invention preferably also includes a label or indicating means capable of signaling the formation of an immunocomplex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{111}$indium or $^{3}H$ The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of $PS_F$ or competent C4BP in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are all incorporated herein by reference.

Thus, in some embodiments, a PS polypeptide, an antibody or a monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides can be used that are well known to those skilled in the art. Exemplary adsorption methods are described herein.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron ($\mu$) to about 5 millimeters (mm) in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein i relation to diagnostic systems are those customarily utilized in diagnostic systems.

E. Assay Methods

The present invention contemplates various assay methods for determining the presence, and preferably amount, of free protein S ($PS_F$) in an aqueous composition such as a biological fluid sample using a polypeptide, polyclonal antibody or monoclonal antibody of this invention as an immunochemical reagent to form an immunoreaction product whose amount relates, either directly or indirectly, to the amount of $PS_F$ in the sample.

Those skilled in the art will understand that there are numerous well known clinical diagnostic chemistry procedures in which an immunochemical reagent of this invention can be used to form an immunoreaction product whose amount relates to the amount of $PS_F$ present in a body sample. Thus, while exemplary assay methods are described herein, the invention is not so limited.

Various heterogenous and homogeneous protocols, either competitive or noncompetitive, can be employed in performing an assay method of this invention.

1. Capture Immunoassay Formats

For example, one embodiment contemplates a method for assaying the amount of $PS_F$ in body fluid sample that utilizes a first capture antibody to capture and immobilize PS in the solid phase and a second indicator antibody to indicate the presence of the captured PS antigen. In this embodiment, one antibody immunoreacts with $PS_F$ to form a $PS_F$-antibody immunoreaction complex, and the other antibody is able to immunoreact with PS while PS is present in the $PS_F$-antibody immunoreaction complex. This embodiment can be practiced in two formats with the immobilized capture antibody being either of the two above-identified antibodies, and the indicator antibody being the other of the two antibodies.

a. Capture Immunoassay Using Immobilized Anti-$PS_F$ Antibody

A capture immunoassay method using an immobilized anti-$PS_F$ antibody molecule for assaying the amount of free PS in a vascular fluid sample comprises the steps of:

(a) Forming an immunoreaction admixture by admixing a fluid sample with an anti-PS antibody of the present invention, preferably a monoclonal antibody. The antibody is present as part of a solid support, i.e., operatively linked to a solid matrix such that the immunoreaction admixture has both a liquid phase and a solid phase, and the antibody functions as a capture reagent.

A preferred anti-PS antibody that immunoreacts with $PS_F$ is an antibody that immunoreacts with the polypeptide represented by a formula selected from the group consisting of: SGIKEIIQEKQNKHC (1:420-434), and CIRSWNLMKQGASIKEIIQEKQNKHC (11:1-26) but does not immunoreact with the polypeptide CTCKPGWQGEKCEFDINECKDPSNINGGCS (1:103-131). Particularly preferred is the monoclonal antibody (MAb 56) produced by the hybridoma LJS 56.

Preferably, the fluid sample is a vascular fluid sample such as blood, or a blood-derived product such as serum or plasma.

(b) The immunoreaction admixture is maintained under biological assay conditions for a predetermined time period such as about 10 minutes to about 16-20 hours at a temperature of about 4° C. to about 45° C. that, such time being sufficient for the PS present in the sample to immunoreact with (immunologically bind) the antibody in the solid phase to form an $PS_F$-containing immunoreaction product (immunocomplex).

Biological assay conditions are those that maintain the biological activity of the immunochemical reagents of this invention and the PS sought to be assayed. Those conditions include a temperature range of about 4° C. to about 45° C., a pH value range of about 5 to about 9 and an ionic strength varying from that of distilled water to that of about one molar sodium chloride. Methods for optimizing such conditions are well known in the art.

(c) The amount of $PS_F$-containing immunoreaction product that formed in step (b) is determined, thereby determining the amount of free PS present in the sample.

Determining the amount of the immunoreaction product, either directly or indirectly, can be accomplished by assay techniques well known in the art, and typically depend on the type of indicating means used.

Preferably, the determining of step (c) comprises the steps of:

(i) admixing the protein S-containing immunoreaction product in the solid phase with a second antibody to form a second immunoreaction admixture having a liquid phase and a solid phase, said second antibody molecule having the capacity to immunoreact with the $PS_F$-containing immunoreaction product.

Antibodies useful as the second antibody include polyclonal antibody preparations raised against purified PS that immunoreact with a variety of epitopes on the PS molecule, or monoclonal antibodies screened for their capacity to bind PS after immunoreaction with an antibody that is specific for $PS_F$ as described herein. Such an antibody immunoreacts with PS whether it is free or complexed with C4BP, and therefore is immunospecific for total PS ($PS_T$). Anti-$PS_F$ antibody molecules do not inhibit protein S binding to C4BP. An exemplary and preferred monoclonal antibody that immunoreacts with PS molecules when immunocomplexed with a $PS_F$-specific antibody is the monoclonal antibody produced by the hybridoma LJS S-7 (MAb S-7).

(ii) maintaining said second immunoreaction admixture for a time period sufficient for said second antibody to complex with the immunoreaction product and form a second immunoreaction product in the solid phase, and (iii) determining the amount of second antibody present in the second immunoreaction product and thereby the amount of immunoreaction product formed in step (c).

In one embodiment, the second antibody is a labelled antibody such that the label provides an indicating means to detect the presence of the second immunoreaction product formed. The label is measured in the second immunoreaction product, thereby indicating the presence, and preferably amount, of second antibody in the solid phase.

Alternatively, the amount of second antibody can be determined by preparation of an additional reaction admixture having an indicating means that specifically reacts with (binds to) the second antibody, as is well known. Exemplary are third immunoreaction admixtures with a labelled anti-immunoglobulin antibody molecule specific for the second antibody. After third immunoreaction, the formed third immunoreaction product is detected through the presence of the label.

b. Capture Immunoassay Using Immobilized Anti-$PS_T$ Antibody

A capture immunoassay method using immobilized anti-$PS_T$ antibody molecules is also contemplated that is related to the capture assay described before. The assay for detecting $PS_F$ comprises the steps of:

(a) Forming a first immunoreaction admixture by admixing a vascular fluid sample with a first anti-protein S antibody containing antibody molecules that immunoreact with $PS_T$. The anti-$PS_T$ antibody operatively linked to a solid matrix such that the first immunoreaction admixture has both a liquid phase and a solid phase. A preferred first antibody is the monoclonal antibody (MAb S-7) produced by the hybridoma LJS S-7.

(b) The immunoreaction admixture is maintained for a time period sufficient to form a protein S-containing immunoreaction product in the solid phase under conditions as previously described.

(c) A second immunoreaction admixture is then formed by admixing the protein S-containing immunoreaction product in the solid phase from step (b) with a second anti-protein S antibody containing antibody molecules immunospecific for $PS_F$, i.e, antibodies of the present invention. A preferred second antibody is the monoclonal antibody (MAb 56) produced by the hybridoma LJS 56.

(d) The second immunoreaction admixture is maintained for a time period sufficient for the $PS_F$-specific antibody molecules to immunoreact with the protein S in the solid phase and form a second protein S-containing immunoreaction product in the solid phase.

(e) The presence, and preferably amount, of product formed in step (d) is then determined, thereby determining the amount of free protein S in the vascular fluid sample.

Determining the presence of the second immunoreaction product can be according to the methods described above for the previous capture immunoassay.

Exemplary capture immunoassays for detecting $PS_F$ are described in Example 6.

2. Competition Immunoassay Formats

Another embodiment for assaying the amount of $PS_F$ in a body fluid sample utilizes a competition reaction in which either a PS polypeptide or an anti-$PS_F$ antibody molecule of this invention is present in the solid phase as an immobilized immunochemical reagent, and the other of the two reagents is present in solution in the liquid phase, in the form of a labeled reagent. A fluid sample is admixed thereto to form a competition immunoreaction admixture, and the resulting amount of label in the solid phase is proportional, either directly or indirectly, to the amount of $PS_F$ in the fluid sample.

Thus one version of this embodiment comprises the steps of:

(a) Forming a competition immunoreaction admixture by admixing a vascular fluid sample with:

(1) an anti-protein S antibody according to this invention containing antibody molecules that immunoreact with $PS_F$, said antibody being operatively linked to a solid matrix such that the competition immunoreaction admixture has both a liquid phase and a solid phase, and (2) a polypeptide of the present invention that is immunoreactive with the added antibody. The admixed polypeptide is operatively linked to an indicating means as described herein.

(b) The competition immunoreaction admixture is then maintained for a time period sufficient for the polypeptide and the $PS_F$ present in the liquid phase to compete for immunoreaction with the solid phase antibody. Such immunoreaction conditions are previously described, and result in the formation of an indicating means-containing immunoreaction product comprising the labeled polypeptide in the solid phase.

(c) The amount of indicating means present in the product formed in step (b) is then determined, thereby determining the presence, and preferably amount, of free protein S in the vascular fluid sample.

Determining the indicating means in the solid phase is then conducted by the standard methods described herein.

Preferred anti-$PS_F$ antibody molecules for use in the competition reaction are the MAb 56 antibody molecules. Also preferred and exemplary is the use of biotinylated polypeptides as described further herein.

Another version of this embodiment comprises the steps of:

(a) Forming a competition immunoreaction admixture by admixing a vascular fluid sample with:

(1) an anti-protein S antibody according to the present invention containing antibody molecules that immunoreact with $PS_F$, and (2) a polypeptide of the present invention that is immunoreactive with the antibody and is operatively linked to a solid matrix such that the competition immunoreaction admixture has both a liquid phase and a solid phase. A preferred antibody is the monoclonal antibody MAb 56.

(b) The competition immunoreaction admixture is then maintained for a time period sufficient for any free PS in the vascular fluid to compete with the admixed antibody molecules for immunoreaction with the solid phase polypeptides and form an antibody-containing immunoreaction product in the solid phase.

(c) The amount of antibody present in the product formed in step (b) is then determined, thereby determining the presence and/or amount of free protein S in the vascular fluid sample.

In preferred embodiments, the antibody is operatively linked to an indicating means such that the determining in step (c) comprises determining the amount of indicating means present in the product formed in step (b). A preferred indicating means is biotinylation as described herein.

Preferably, the vascular fluid sample is provided to a competition immunoreaction admixture as a known amount of blood, or a blood derived product such as serum or plasma. Further preferred are embodiments wherein the amount of immunochemical reagent in the liquid phase of the immunoreaction admixture is an excess amount relative to the amount of reagent in the solid phase. Typically, a parallel set of competition immunoreactions are established using a known amount of purified PS in a dilution series so that a standard curve can be developed, as is well known. Thus, the amount of product formed in step (c) when using a vascular fluid sample is compared to the standard curve, thereby determining the amount of $PS_F$ present in the vascular fluid.

In another embodiment, the present invention contemplates a competition reaction assay that utilizes the binding interaction between C4BP and a PS polypeptide of the present invention as the basis for a diagnostic assay of $PS_F$ in a vascular fluid sample. This embodiment comprises the steps of:

(a) Forming a competition reaction admixture by admixing a vascular fluid sample with:

(1) a solid support having affixed thereto purified C4BP such that the competition reaction admixture has both a liquid phase and a solid phase, and (2) a PS polypeptide of the present invention that has the capacity to bind to C4BP and inhibit protein S binding to C4BP. The admixed polypeptide is operatively linked to an indicating means as described herein. A preferred indicating means is biotinylated polypeptide. Particularly preferred polypeptide for use herein are polypeptides PSP-12 and PSP-loop due to their demonstrated binding to C4BP as shown in the Examples. C4BP can purified as described herein, and thereafter affixed to a solid matrix by adsorption from a solution as described herein.

(b) The competition reaction admixture is then maintained for a time period sufficient for the polypeptide and the $PS_F$ present in the liquid phase to compete for binding with the solid phase C4BP. Such reaction conditions compatible with protein S binding to C4BP in the solid phase are described elsewhere herein, and result in the formation of an indicating means-containing reaction product comprising the labeled polypeptide complexed with C4BP in the solid phase.

(c) The amount of indicating means present in the product formed in step (b) is then determined as previously described, thereby determining the presence, and preferably amount, of free protein S in the vascular fluid sample.

Competition reactions are preferably conducted with standard curves as described above in order to more accurately determine the amount of $PS_F$ in the vascular fluid sample.

In a related embodiment, the above competition reaction for detecting $PS_F$ that utilizes immobilized C4BP can be practiced with an anti-$PS_F$ antibody of the present invention in place of a PS polypeptide in the liquid phase because both the recited PS polypeptide and the anti-PS, antibody bind C4BP and thus can compete with $PS_F$ in the vascular fluid sample for binding to the immobilized C4BP. In this embodiment, the antibody is preferably operatively linked to an indicating means as described before to facilitate detection of the competition reaction product.

3. Competition Immunoassays Specific for Competent C4b Binding Protein

The present invention also contemplates competition immunoreactions similar to those previously described that are adapted for the determination of the presence, and preferably amount, of competent C4b binding protein (C4BP) in a fluid sample.

"Competent C4BP" is C4BP in a form that has the capacity to bind to free protein S ($PS_F$) in solution. Forms of C4BP not able to bind $PS_F$ include C4BP already complexed with $PS_F$, defective C4BP due to improper assembly of its subunits or the presence of genetically deficient protein subunits, and the like. Competent C4BP levels in the blood are important because it is the form of C4BP that contributes to inactivation of $PS_F$ by complex formation, and therefore the determination of plasma levels of competent C4BP provides clinically relevant information.

The competition assay is based on the binding interaction disclosed herein between a PS polypeptide of the present invention and C4BP.

Thus, in one embodiment the present invention contemplates a method for determining the amount of C4BP in a fluid sample, preferably a vascular fluid sample such as plasma, comprising the steps of:

(a) forming a binding reaction admixture by admixing a vascular fluid sample with a protein S polypeptide of this invention, said polypeptide being operatively linked to a solid matrix such that the binding reaction admixture has both a liquid phase and a solid phase;

(b) maintaining said binding reaction admixture for a time period sufficient for any competent C4 binding protein present in the vascular fluid sample to bind to the polypeptide and form a C4b binding protein-containing reaction product in the solid phase; and (c) determining the amount of C4b binding protein present in the solid phase reaction product. Typical binding reaction conditions suitable for use are described in the Examples.

In preferred embodiments, the determining step for detecting solid phase C4BP comprises the steps of:

(i) admixing the reaction product formed in step (b) with an anti-C4b binding protein antibody containing antibody molecules that immunoreact with C4b binding protein to form an immunoreaction admixture;

(ii) maintaining said immunoreaction admixture for a time period sufficient for the antibody to immunoreact with any C4b binding protein present in the solid phase and form a solid phase immunoreaction product; and (iii) determining the amount of antibody present in the solid phase immunoreaction product formed in step (ii), and thereby the amount of competent C4b binding protein in the vascular fluid sample. The admixing, maintaining and determining steps can be carried essentially as described elsewhere herein.

An anti-C4BP binding protein antibody suitable for use in step (i) can be any antibody that immunoreacts with C4BP when it is complexed with PS. A preferred anti-C4BP antibody is a polyclonal antisera prepared by immunization of rabbits with a purified C4BP preparation. Particularly preferred are antibodies containing antibody molecules that immunoreact with the alpha subunit of C4BP, which can be prepared by immunization with purified alpha subunit as is well known, or can be obtained from a variety of commercial sources. Methods for screening for an anti-C4BP antibody molecule that binds C4BP when it is present in a PS:C4BP complex include the binding assays described herein following routine preparation of a monoclonal antibody using C4BP as the immunogen.

In preferred embodiments, the antibody in the solid phase is detected by the presence of an indicating means in the immunoreaction product, such as where the antibody is a labeled antibody.

In another embodiment, the present invention contemplates a method for determining the amount of C4BP in a fluid sample, preferably a vascular fluid sample such as plasma, comprising the steps of:

(a) forming a binding reaction admixture by admixing a vascular fluid sample with:

(i) a protein S polypeptide of the present invention, and (ii) an anti-C4b binding protein antibody containing antibody molecules that immunoreact with C4b binding protein, said antibody being operatively linked to a solid matrix such that the immunoreaction admixture has both a liquid phase and a solid phase;

(b) maintaining said immunoreaction admixture for a time period sufficient for any competent C4b binding protein present in the vascular fluid sample to bind to the antibody and form an immunoreaction product in the solid phase, and for the polypeptide to bind to said immunoreaction product; and (c) determining the amount of polypeptide present in the solid phase reaction product, and thereby the amount of competent C4b binding protein.

Preferably, the antibody contains antibody molecules that immunoreact with the alpha subunit of the C4b binding protein as described before.

A preferred means for determining the amount of solid phase reaction product is by the use of a labeled PS polypeptide, followed by the detection means described herein for other labeled products in the solid phase. Particularly preferred are the use of biotinylated PS polypeptides.

Exemplary assay methods adaptable to the present methods for detecting competent C4BP are described at least in the Examples herein.

Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

G. Therapeutic Compositions

The present invention contemplates therapeutic compositions useful for practicing the therapeutic methods described herein. Therapeutic compositions of the present invention contain a physiologically tolerable carrier together with a therapeutic reagent of this invention, namely a PS polypeptide, an anti-PS antibody or monoclonal antibody as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an amount of a PS polypeptide or anti-PS; antibody molecule of the present invention sufficient to inhibit protein S binding to C4BP. Typically this is an amount of at least 0.1 weight percent, and more preferably is at least 1 weight percent, of peptide or antibody per weight of total therapeutic composition. A weight percent is a ratio by weight of peptide or antibody to total composition. Thus, for example, 0.1 weight percent is 0.1 grams of PS polypeptide per 100 grams of total composition.

H. Therapeutic Methods

It has been discovered that the PS polypeptides, antibodies, and monoclonal antibodies of the present invention (i.e., PS:C4BP complex formation inhibitors) have the capacity to inhibit PS binding to C4BP. In view of C4BP's physiological role in complexing with PS and thereby inactivating its anticoagulative effects, the present PS:C4BP complex formation inhibitors are useful for inhibiting protein S binding to C4BP in vivo.

Thus, in one embodiment, the present invention provides a method for inhibiting protein S binding to C4BP in a patient comprising administering the patient a therapeutically effective amount of a physiologically tolerable composition containing a PS polypeptide, anti-$PS_F$ antibody or monoclonal antibody of the present invention.

A therapeutically effective amount of a PS polypeptide is a predetermined amount calculated to achieve the desired effect, i.e., to inhibit protein S binding to C4BP in vivo in a patient, and thereby increase the effective vascular concentration of $PS_F$ in the patient.

The in vivo inhibition of PS binding to C4BP using a PS polypeptide of this invention is a particularly preferred embodiment and is desirable in a variety of clinical settings, such as where the patient is exhibiting symptoms of coagulation or is at risk for thrombosis. Typically, a therapy for inhibiting protein S binding to C4BP using PS polypeptides will be indicated when a patient exhibits elevated plasma levels of C4BP, disseminated intravascular coagulation (DIC), septic shock, venous or arterial thrombosis and the like conditions requiring anticoagulant intervention.

A therapeutically effective amount of a PS polypeptide of this invention is typically an amount of PS polypeptide such that when administered in a physiologically tolerable composition is sufficient to achieve a plasma concentration of from about 0.1 micromolar ($\mu$M) to about 100 $\mu$M, and preferably from about 0.5 $\mu$M to about 10 $\mu$M.

A therapeutically effective amount of an antibody of this invention is typically an amount of antibody such that when administered in a physiologically tolerable composition is sufficient to achieve a plasma concentration of from about 0.1 microgram ($\mu$g) per milliliter (ml)

to about 100 μg/ml, preferably from about 1 μg/ml to about 5 μg/ml, and usually about 5 μg/ml.

The level of inhibition of protein S binding to C4BP present in a patient indicative of the efficacy of the present therapy can be readily determined by routine clinical analysis that detects plasma levels of free protein S. Exemplary assays to monitor the level of $PS_F$ are described herein. Alternatively, the effectiveness of the therapy can be determined by observing the anticoagulant effects of the therapy.

The therapeutic compositions containing PS polypeptide or antibody of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are particular to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective therapeutic amounts of a PS polypeptide, antibody, or monoclonal antibody, a diagnostic method of this invention for detecting a PS polypeptide, antibody, or monoclonal antibody, respectively, in the subject's blood is useful to characterize the fate of the administered therapeutic composition.

I. Immunoaffinity Purification of Free Protein S

The specificity of an anti-$PS_F$ antibody of the present invention for immunoreaction with free PS and not with PS:C4BP complex provides a useful reagent for purifying free PS from an aqueous solution such as a complex biological fluid including blood, plasma, plasma-derived fluids and the like sources of free PS. Additional sources of free PS from which to purify free PS by the present methods include homogenized tissues, cell cultures and expression systems for producing PS using recombinant DNA methods for expressing cloned genes that encode PS.

Extremely pure $PS_F$ can be prepared using the methods herein, and such a preparation is useful for therapeutic administration of "anticoagulant active" PS, namely $PS_F$, in cases of protein S deficiency and as an anticoagulant and antithrombotic. Insofar as the reagents described herein do not bind PS:C4BP, the present methods allow the preparation of $PS_F$ that is not contaminated by C4BP in any form, which could counteract the beneficial anticoagulative effects of $PS_F$ by binding and inactivating $PS_F$.

Thus the present invention also contemplates a method for purifying free protein S ($PS_F$) from an aqueous solution comprising the steps of:

(a) admixing an aqueous solution that contains $PS_F$ with an antibody of the present invention that contains antibody molecules that immunoreact with $PS_F$ to form an immunoreaction admixture;

(b) maintaining the immunoreaction admixture under immunoreaction conditions for a time period and under sufficient for the $PS_F$ in solution to immunoreact with the antibody and form an immunoreaction product; and (c) isolating the immunoreaction product from the remainder of the immunoreaction admixture, thereby recovering the immunoreacted $PS_F$ away from the contaminants present in the initial aqueous solution, thereby forming purified $PS_F$.

In preferred embodiments, the antibody molecules admixed in step (a) are immobilized antibody molecules, that is they are operatively linked to a solid support as described further herein. Where an immobilized antibody is used, the immunoreaction admixture has both a solid phase and a liquid phase, and the resulting immunoreaction product is formed in the solid phase. This provides a particularly preferred advantage in purification, because the solid support can be conveniently washed or rinsed with buffers formulated to specifically elute/remove macromolecules in the matrix of the solid support and surrounding the support that are not specifically immunoreacted with (bound by) the immobilized antibody molecules. After the wash to elute non-specifically immunoreacted macromolecules, the immobilized antibody molecules are contacted with a buffer formulated to specifically remove (elute) the immunoreacted $PS_F$, the eluted free PS molecules of which are collected (recovered) in a substantially purified form.

In one embodiment, the elution buffer can contain a polypeptide in the liquid phase that immunoreacts with the antibody in the solid phase and acts as a competitor for immunoreaction with $PS_F$. In another embodiment, the release buffer can contain salts incompatible with the formation of a $PS_F$-antibody immunoreaction complex. Reagent conditions compatible with formation of the immunoreaction product, with wash buffer, or with the elution buffer can readily be developed by one skilled in the art using the assays and reagents described herein.

Stated differently, the present method for producing purified $PS_F$ involves two steps.

The first step involves immunoabsorption (adsorption) of $PS_F$ from an aqueous solution. The adsorbent comprises an immobilized antibody composition, namely an antibody of this invention bound to a suitable substrate such as agarose beads or the like solid support. After the $PS_F$ is adsorbed to the immobilized antibodies by specific immunoreaction, the adsorbed material is washed extensively with a buffer to removed non-immunoreacted materials, macromolecules, proteins and the like.

The second step involves a treatment step (elution) to specifically remove (elute) the immunoreacted (adsorbed) material with a buffer formulated to perturb the immunoreaction product in the solid phase and effect release of the immunoreacted antigen into the liquid phase of the elution buffer. Buffers useful for eluting specifically immunoreacted proteins from immobilized antibody columns are generally well known. Exemplary buffers are described in Example 6.

Methods for preparing an immobilized antibody molecule composition, for immunoreacting specific proteins, and for their elution therefrom to produce purified proteins are generally well known in the art and are also described further herein. For example, see the teaching of Zimmerman et al. in U.S. Pat. No. 4,361,509, the teachings of which are hereby incorporated by reference, that describes the immunoaffinity purification of Factor VIII from plasma sources using an immobilized monoclonal antibody molecule. Exemplary immobilized antibody molecules, their use and their preparation are described in Example 6.

Particularly preferred are methods utilizing the $PS_F$-specific antibody molecules of the monoclonal antibody MAb 56 immobilized to agarose beads as described in Example 6.

In a related embodiment, the present invention also contemplates a composition for purifying $PS_F$ from aqueous solutions according to the methods described herein. The composition comprises antibody molecules of the present invention immunospecific for $PS_F$ in the form of immobilized antibody molecules, i.e., operatively linked to a solid support. Exemplary compositions are described in Example 6, utilizing agarose beads having affixed thereto (operatively inked) either polyclonal or monoclonal antibodies of the present invention. Particularly preferred are antibody molecules that immunoreact with the preferred polypeptides, PSP-12 and PSP-loop, and more preferred is the monoclonal antibody MAb 56.

EXAMPLES

The following description provides details of the manner in which particular embodiments of the present invention may be made and used. This description, while exemplary of the present invention, is not to be construed as specifically limiting the invention. Variations and equivalents, now known or later developed, which would be within the understanding and technical competence of one skilled in this art are to be considered as falling within the scope of this invention.

1. Polypeptides

Overlapping synthetic protein S peptides listed in Table 1 above were produced by the simultaneous multiple peptide synthesis method using the solid-phase technique described by Houghten, *Proc. Natl. Acad. Sci. U.S.A.*, 82:5131-5135 (1985). The peptides are hereinafter referred to by their polypeptide designations as listed in Table 1. The amino acid residue sequence and corresponding SEQ ID NO for each peptide are also listed in Table 1. All peptides were synthesized in the carboxy-terminal amide form. The synthesized peptides were then analyzed by reverse phase high performance liquid chromatography (HPLC) on a Vydac C-18 column (Alltech Associates, Inc., Ill.) with a 0–60% acetonitrile linear gradient in 0.1% trifluoroacetic acid. Peptides were then purified to homogeneity by preparative HPCL using optimal conditions suggested by the analytical chromatography. In order to prevent disulfide formation among peptides, in some peptides the originally occurring cysteine was substituted by a serine or a glycine amino acid residue as indicated in Table 1. Amino acid compositions and concentrations of isolated peptides were determined by subjection to 24 hour hydrolysis in 6N HCl in evacuated tubes at 110° degrees Celsius (110° C.) and subsequent analysis on a Beckman Model 6300 High Performance Analyzer. The peptides, PSP-loop, PSP-424K and PSP-428K, were not subjected to HPLC purification and thus, were only 30% pure.

To verify the correct molecular weight mass spectroscopic analyses of peptides PSP-12 (1:420–434) and PSP-605 (1:605–614) using the FIB positive ion mass spectra obtained on a VG-ZAB-VSE double focusing mass spectrometer equipped with a cesium ion gun yielded a single peak and the exact expected molecular weight of 1755 for the single protonated form of PSP-12 and 1072 for the single protonated form of PSP-605.

Purified peptides were separately resuspended in distilled water to form a dissolved peptide solution at a final concentration of 2.5 mM. Subsequently, one-tenth volume of 10-fold concentrated buffer referred to as TBS-Az containing 0.05M Tris hydroxymethyl aminomethane-hydrochloride (Tris-HCl) at pH 7.4 0.1M sodium chloride (NaCl), 0.02% sodium azide ($NaN_3$). The pH of the solution was checked, and if necessary, adjusted to pH 7.4 with titrated amounts of 1M Tris-base. For peptides that appeared to be not completely soluble at 2.5 mM in TBS-Az, the partially dissolved peptide suspensions separately were centrifuged at 13,000×g to pellet the insoluble material. The molar concentrations in the resultant individual supernatants were estimated from the absorbance at 280 nm and 257 nm, respectively, for peptide solutions containing aromatic amino acids using a molar extinction coefficient of 5,600 $M^{-1}cm^{-1}$ for tryptophan and 1,400 $M^{-1}cm^{-1}$ for tyrosine at 280 nm, using a molar extinction coefficient of 200 $M^{-1}cm^{-1}$ for phenylalanine at 257 nm.

2. Preparation of Polyclonal Antisera to Synthetic Polypeptides

A. Preparation of Immunogen

For preparation of a peptide immunogen, the synthetic polypeptide PSP-12 was prepared as described in Example 1. The synthesized peptide PSP-12 was coupled to keyhole-limpet-hemocyanin (KLH) (Sigma, St. Louis, Mo.) using the heterobifunctional crosslinking agent, N-succinimidyl-3-(2-pyridyldithio) propionate (SPDP) (Pierce Biochemicals, Rockford, Ill.). For the coupling procedure, 80 microliters (μl) of 10 milligrams/milliliter (mg/ml) SPDP dissolved in dimethylformamide were admixed dropwise to 400 μl 15 mg/ml KLH in 0.1M phosphate, 0.1M NaCl at pH 8.5 under continuous stirring conditions for 30 minutes at 22° C. in order to form SPDP-activated KLH. The resultant SPDP-activated KLH was then extensively dialyzed at 4° C. against a buffered solution of 0.1M phosphate and 0.1M NaCl at pH 7.4 in order to remove uncoupled SPDP. Six mg of prepared peptide PSP-12 having a C-terminal cysteine were first dissolved in 2 ml of 0.1M phosphate and 0.1M NaCl at pH 7.4 and then admixed with SPDP-activated KLH prepared above under continuous stirring conditions. The degree of coupling of PSP-12 with KLH was monitored by diluting an aliquot of the mix 1:100 at time zero, and each hour thereafter, and measuring the release of pyridine-2-thione at 343 nm in a spectrophotometer. The end point of coupling was determined to be an increase of 0.2 in absorbency, or upon visualization of precipitate at which point KLH conjugates peptide was formed, and designated PSP-12-KLH immunogen.

B. Immunization and Collection of Polyclonal Antisera

To form anti-peptide antibodies, the PSP-12-KLH immunogen prepared in Example 2a was emulsified using Adjuvant Complete Freund (DIFCO Laboratories, Detroit, Mich.) for the first injection and Adjuvant Incomplete Freund (DIFCO) for all subsequent injections according to the manufacturer's instructions, and the PSP-12-KLH immunogen was incorporated into the emulsion at a concentration of 2 mg/ml. One-half ml of a prepared emulsion was injected subcutaneously into each of two New Zealand white rabbits after pre-immune serum samples were collected. The rabbits were injected three times at weekly intervals following the injection protocol as detailed. Two weeks after the last injection, blood samples were collected to check antibody titer against the specific peptide PSP-12 used as an immunogen by the ELISA assay described below in Example 2C. The collected blood samples were stored at 4° C. for 12 hours, after which the samples were centrifuged at 3000×g for 20 minutes. The resultant supernatant containing anti-peptide antibodies was collected, designated polyclonal anti-peptide (anti-PS) antibodies and stored at −20° C.

Peptides: PSP-54, PSP-561, PSP-418*, PSP-13*, and PSP-14* were also separately prepared as immunogens by conjugation with KLH as described in Example 2A. Immunization of separate rabbits for the production of antisera against each of the peptides listed above was performed as described herein. The resultant antisera were then screened by ELISA as described for anti-PSP-12 (also referred to as anti-PS (420–434)) antisera in Example 2C.

C. ELISA to Screen Antisera Immunoreactivity

The peptide antibody titers and immunospecificity in sera collected from rabbits in Example 2B were determined in an enzyme-linked-immunosorbent-assay (ELISA) as described below. The antigens used in the ELISA included the immunizing peptide PSP-12 and purified human protein S (PS). Purified human protein S was prepared as described in Schwarz et al., *Blood*, 64:1297–1300 (1984), the disclosure of which is hereby incorporated by reference.

To determine the immunospecificity of the rabbit antisera obtained in Example 2B, ELISA assays were performed. Briefly, 50 µl of 50 µM concentrations of peptides PSP-12, PSP-loop, PSP-424K and PSP-428K prepared in Example 1 and listed in Table 1 or 10 µg/ml of PS prepared in Example 2C in a buffer consisting of 0.05M sodium carbonate ($Na_2CO_3$) and 0.02% $NaN_3$ at pH 9.0 were separately admixed into the wells of microtiter plates. The plates were maintained at 37° C. for one hour to permit the antigens to become operatively affixed to the well walls. After washing the antigen-coated wells with TBS, the wells were blocked with 250 µl/well of 10% bovine serum albumin (BSA) (Sigma) in TBS for one hour at 22° C. The blocking solution was then removed and the wells were subsequently washed five times with 250 µl/well of maintenance buffer (0.05M Tris-HCl, 0.1M NaCl, 0.02% $NaN_3$, 1 mg/ml BSA, 5 mM $CaCl_2$, 0.01% Tween 20 at pH 7.4).

Fifty µl of rabbit nonimmune or specific antiserum serially diluted in maintenance buffer were then admixed to the washed wells to form an immunoreaction admixture, that was maintained for one hour at 37° C. to allow formation of a solid-liquid phase immunoreaction products. The wells were then washed three times with maintenance buffer followed by admixture of 50 µl of 1.0 µg/ml of secondary antibody (polyclonal biotinylated goat-anti-rabbit-IgG) (Pierce Biochemicals) diluted in maintenance buffer to each well for the detection of immunoreactant products. The plates were maintained for 1 hour at 37° C. after which time the secondary antibody solution was removed.

After washing the wells as described above, 50 µl of 1.0 µg/ml streptavidin-alkaline-phosphatase (Pierce Biochemicals) in maintenance buffer were admixed into each well and maintained for 30 minutes at 37° C. Detection of specific immunoreaction products was obtained by admixture of 150 µl/well of 5 mg/ml p-nitrophenylphosphate (PNPP) (Pierce Biochemicals) in 0.1M diethanolamine and 0.02% $NaN_3$ at pH 9.0 followed by measurement of the change in absorbance at 405 nm over time using the EL312 Microplate Bio-Kinetics Reader and the KinetiCalc Software Program (Biotek Instruments, Inc., Vt.). Nonspecific binding was considered as the measured absorbance in 10% BSA blocked wells which served as negative controls without the preceding coating of a specific protein or peptide. Under the described conditions, nonspecific binding never exceeded more than 5% of the specific binding. Rabbit anti-peptide antisera which exhibited immunoreactivity that produced an optical density change at 405 nm of greater than 20 delta per minute using the kinetic program as compared to the immunoreactivity of pre-immune serum toward peptides PSP-12, PSP-loop, PSP-424K and PSP-428K and that similarly immunoreacted with PS, was selected for use as an anti-peptide antibody, and also selected for further purification as described in Example 3.

Rabbit antisera, that were obtained in Example 2b against the peptides: PSP-54, PSP-561, PSP-418*, PSP-13* and PSP-14*, were screened for immunoreactivity to the respective peptide immunogens and PS as described above. Rabbit antisera which exhibited significant immunoreactivity as compared to the pre-immune sera toward each of the peptide immunogens and PS were further purified and analyzed as described in Example 3.

3. Purification of Anti-PS Antibody, Anti-PS(420–434) (Anti-PSP-12)

Purification of the IgG fraction from rabbit antiserum, which showed significant reactivity towards the immunizing peptide-PSP-12 and towards the peptides PSP-loop, PSP-424K and PSP-428K as well as purified PS, was conducted by ammonium-sulfate precipitation (0–45%), followed by purification of IgG on an ion-exchange Mono Q column (Pharmacia LKB, Piscataway, N.J.) connected to a fast protein liquid chromatography (FPLC) system (Pharmacia). Immunoaffinity purification of the pooled immunoreactive IgG-fraction was performed by passing approximately 100 mg of the IgG over a 5 ml column containing 3 mg of protein S prepared in Example 2C coupled to Sepharose 4B (Pharmacia) as described in Example 2A. After a thorough washing of the column with 5 column volumes of 0.05M Tris-HCl and 1M NaCl at pH 7.4 to remove unbound antibodies, the bound IgG was eluted with two column volumes of 0.1M glycine-HCl at pH 2.5. The eluted protein was monitored by absorbance at 280 nm and the IgG concentrations determined from the extinction coefficient of 13.5. The eluted IgG was immediately dialyzed against TBS-Az, concentrated against 50% sucrose for approximately 3–4 hours and once more extensively dialyzed against TBS-Az to a final concentration of 3–4 mg/ml. Analysis by 4–15% sodium dodecyl sulfate-polyacrylamide gel electrophoresis (SDS-PAGE) of reduced and non-reduced samples revealed greater than 95% pure IgG. This immunoaffinity- purified anti-peptide antibody is designated anti-PS(420–434) for use in this invention.

A. Direct Binding of PS to Anti-PS(420–434) Antibody

The affinity of immunoaffinity purified anti-PS(420–434) antibody towards PS was determined by measuring the direct binding in solid-phase ELISA of biotinylated (b-PS) to immobilized anti-PS(420–434) antibody. For the ELISA assay, 50 μl of anti-PS(420–434) antibody diluted to a concentration of 10 μg/ml in 0.05M Na₂CO₃ and 0.02% NaN₃ at pH 9.0 were admixed to wells of a microtiter plate and maintained for one hour at 37° C. to form antibody-coated wells. Following the removal of the antibody solution at the end of the maintenance period, 250 μl of 10% BSA in TBS-Az at pH 7.4 were admixed into each well for one hour at 22° C. to block unoccupied sites on the wells. For wells which were used as negative controls, the antibody coating step was omitted prior to the blocking step. The antibody-coated and blocked wells were then washed three times with maintenance buffer prepared as described in Example 2C. Fifty μl of b-PS, prepared by combining biotin (Clontech, Palo Alto, Calif.) with purified PS (Example 2C) following the manufacturer's instructions, diluted in maintenance buffer to concentrations ranging from 0 to 10 μg/ml were admixed into the washed wells to form an immunoreaction admixture that was maintained for one hour at 37° C. to form an immunoreaction product in the solid phase. The wells were subsequently washed five times with maintenance buffer. The detection and measurement of specific immunoreaction products was accomplished by admixture of streptavidin-alkaline-phosphatase followed by PNPP as described previously for the ELISA in Example 2C.

The results of the ELISA-analysis indicated that the anti-PS(420–434) antibodies bound native PS with a dissociation constant ($K_d$) of 10 nanomoles (nM).

A similar assay in which anti-PS(603–616) was adsorbed in the solid-phase and b-PS was admixed in concentrations ranging from 0–40 μg/ml yielded a single class of binding sites with a dissociation constant ($K_d$) of 31 nM.

Thus, polyclonal antibodies raised against the most potent inhibitory peptide PSP-12 (1:420–434), as described in Example 5 that were immunoaffinity-purified on a PS-Sepharose column, immunoreacted with native PS. Thus, at least parts of the region represented by this peptide in PS were exposed and available for interaction with other molecular species at the solvent-accessible surface of PS. Antibodies produced against small synthetic peptides have been shown to be capable of recognizing native protein.

4. Preparation of Monoclonal Antibodies

A. Preparation of Hybridoma LJS-56

The polypeptide designated PSP-12 (1:420–434) was prepared as an immunogen according to Example 2a. Balb/c ByJ mice (Scripps Clinic and Research Foundation Vivarium, La Jolla, Calif.) were immunized intraperitoneally (i.p.) with 50 μg of prepared PSP-12-KLH immunogen in complete Freund's adjuvant (CFA) followed by a second and third immunization using the same PSP-12-KLH immunogen, each about three weeks apart, in incomplete Freund's adjuvant (IFA). The mice received a boost of 50 μg of the prepared peptide intravenously (i.v.) in normal saline 4 days prior to fusion and a second similar perfusion boost one day later.

The animals so treated were sacrificed and the spleen of each mouse was harvested. A spleen cell suspension was then prepared. Spleen cells were then extracted from the spleen cell suspension by centrifugation for about 10 minutes at 1000 rpm, at 23° C. Following removal of the resultant supernatant, the cell pellet was resuspended in 5 ml cold ammonium chloride (NH₄Cl) lysing buffer, and was maintained for about 10 minutes.

Ten ml of Dulbecco's Modified Eagle Medium (DMEM) (GIBCO) and HEPES [4-(2-hydroxyethyl)-1-piperidineethanesulfonic acid]buffer were admixed to the lysed cell suspension to form an admixture, and that admixture was centrifuged for about 10 minutes at 1000 rpm at 23° C.

After the resultant supernatant was decanted, the pellet was resuspended in 15 ml of DMEM and HEPES and was centrifuged for about 10 minutes at 1000 rpm at 23° C. The above procedure was repeated.

The pellet was then resuspended in 5 ml DMEM and HEPES. An aliquot of the spleen cell suspension was then removed for counting. Fusions were accomplished in the following manner using the non-secreting mouse myeloma cell line P3X63Ag 8.653.1, a subclone of line P3x63Ag 8.653 (ATCC 1580). With a myeloma to spleen cell ratio of about 1 to 10 or about 1 to 5, a sufficient quantity of myeloma cells were centrifuged into a pellet, washed twice in 15 ml DMEM and HEPES, and then centrifuged for 10 minutes at 1000 rpm at 23° C.

Spleen cells and myeloma cells were combined in round bottom 15 ml tubes. The cell mixture was centrifuged for 10 minutes at 1000 rpm at 23° C. and the supernatant was removed by aspiration. Thereafter, 200 μl of 50 percent (weight per volume) aqueous polyethylene glycol 4000 molecular weight (PEG); (ATCC Baltimore, Md.) at about 37° C. were admixed with the pellet using a 1 ml pipette with vigorous stirring to disrupt the pellet. The cells were then gently mixed for between 15 and 30 seconds. The resultant cell mixture was centrifuged 4 minutes at 700 rpm.

At about 8 minutes from the time of adding the PEG, 5 ml of DMEM plus HEPES buffer were admixed slowly to the pellet, without disturbing the cells. After 1 minute, the resulting admixture was broken up with a 1 ml pipette and was maintained for an additional 4 minutes. This admixture was centrifuged for 7 minutes at 1000 rpm. The resultant supernatant was decanted, 5 ml of HT (hypoxanthine/thymidine) medium were slowly admixed to the pellet, and the admixture was maintained undisturbed for 5 minutes. The pellet was then broken into large chunks and the final cell suspension was placed into T75 flasks (2.5 ml per flask) into which 7.5 ml HT medium had been placed previously. The resulting cell suspension was maintained at 37° C. to grow the fused cells. After 24 hours 10 ml of HT medium were admixed to the flasks followed 6 hours later by admixture of 0.3 ml of 0.04 mM aminopterin. Forty-eight hours after fusion, 10 ml of HAT (hypoxanthine/aminopterin/thymidine) medium were admixed to the flasks.

Three days after fusion, viable cells were plated out in 96-well tissue culture plates at about $2 \times 10^4$ viable cells per well (768 total wells) in HAT buffer medium as described in Kennett et al., *Curr. Top. Microbiol. Immunol.*, 81:77 (1978). The cells were fed seven days after fusion with HAT medium and at approximately 4–5 day intervals thereafter as needed with HT medium. Growth was followed microscopically and culture supernatants were collected about two weeks later. The culture supernatants from HAT resistant cultures were subsequently assayed for the presence of PSP-12 (1:420-434) specific antibody by solid-phase ELISA as described in Example 2C and selected as hybridomas that produce an antibody of this invention. Hybridoma cultures producing anti-PS(420-434) monoclonal antibodies were identified thereby and one clone was designated LJS 56 (or MAb 56).

B. Immunoscreening of Monoclonal Antibodies by ELISA

Monoclonal antibody 56 (MAb 56) was screened for further immunospecificity as in Example 2C using the peptides PSP-12, PSP-loop, PSP-424K and PSP428K in the solid-phase. By those methods, it was determined that MAb 56 bound to all of the peptides saturating in a dose-dependent manner. The binding of MAb 56 to the PSP-loop peptide saturated at an antibody concentration of approximately 0.6 µg/ml. This was in contrast to that seen with peptides PSP-12, PSP-424K and PSP-428K where 1.2 µg/ml of MAb 56 was necessary for saturation of the binding sites. MAb 56 did not bind to a peptide corresponding to PSP-I2 synthesized in the reverse order. In addition, MAb 56 failed to bind to peptides that had a negatively charged glutamic acid amino acid substitution for a normally occurring positively charged lysine at either amino acid residue positions 423 and 432 of the native protein S sequence. Thus, MAb 56 bound to peptides in a residue- and conformation-specific manner. In addition, MAb 56 was also found to immunoreact with solid phase protein S in the assay described in Example 2C.

The specificity of purified MAb 56 towards either free protein S or total protein S was further evaluated as described in Example 6. The MAb 56, specific for peptide PSP-12, was also shown thereby to immunoreact with free protein S, and to not immunoreact with PS:C4BP complex.

A direct binding assay in which MAb 56 was coated to the wells of microtiter plates as described in Example 3 and admixed with native b-PS confirmed that immobilized MAb 56 binds native PS.

Thus, because MAb 56 is specific for the peptide PSP-12, and binds only free, not complexed, protein S, it is a preferred monoclonal antibody for the present invention. However, other monoclonal antibodies functionally equivalent to MAb 56 were produced using the PSP-12-KLH conjugate as the immunogen. One such MAb is LJS-418 (MAb 418) and it displays a binding affinity for protein S similar to that of MAb 56. Other monoclonal antibodies can similarly be produced using the other PS polypeptides of this invention.

C. Purification of Monoclonal Antibody

Hybridomas secreting anti-PS(420-434) antibodies as described in Example 4A were injected into 10-week old Balb/c mice as described below to produce ascites fluid.

To that end, separate sets of 10-week old Balb/c mice were primed with 0.3 ml of mineral oil and then injected intraperitoneally with $5 \times 10^6$ hybridoma cells. The average time for development of ascites was 9 days. Following clarification by centrifugation at $15,000 \times g$ for 15 minutes at 23° C., ascites fluids produced by hybridomas were pooled and stored frozen at −20° C. to form monoclonal antibody compositions.

The ascites-produced monoclonal antibodies were further purified by fast protein liquid chromatography (FPLC) using a Pharmacia Mono Q HR5/5 anion exchange column (Pharmacia) using a 0–0.5M NaCl gradient in 10 mM Tris-HCl at pH 8.0 following directions supplied with the column. The FPLC-treated MAbs were then concentrated using an Amicon stirred ultrafiltration cell (Amicon, Danvers, Ma.; PM 30 membrane) to a concentration of 1 mg/ml, dialyzed into TBS and stored at −70° C. to form purified MAb.

5. Inhibition of Protein S Binding to C4BP

A. Competition Binding Assay Using C4BP in Solid Phase i) Purification of C4BP

Purified human C4BP was obtained from 5 liters (l) of human citrated plasma by precipitation with 80 mM of barium chloride in presence of inhibitors, benzamidine hydrochloride (10 mM), diisopropylphosphorofluoridate (1 mM), phenylmethanesulphonyl fluoride (1 mM) and soybean trypsin inhibitor (50 mg/l). After stirring the mixture for 1 hr, the barium citrate precipitate was sedimented by centrifugation at $5000 \times g$ for 10 minutes at 4° C. The precipitate was resuspended in 700 ml of 0.2M ethylenediaminotetraacetic acid (EDTA) pH 7.4 and extensively dialyzed against TBS-Az with 10 mM benzamidine hydrochloride and passed through a column (1.5×40 cm) containing 3 mg IgG/ml gel of immunopurified anti-C4BP rabbit polyclonal antibodies (CalBiochem, San Diego, Calif.) coupled to CNBr activated Sepharose 4B, with a flow rate of 35 ml/hr. The beads were washed with 100 ml of TBS containing 1M NaCl followed by 100 ml of 20 mM EDTA in TBS. The C4BP antigen was eluted with 100 ml of 3M guanidine-hydrochloride in TBS and 2 ml/fractions were collected. The fractions were analyzed for the presence of C4BP by SDS-PAGE as described below, were pooled (52 ml), and the protein was concentrated using PM 30 Diaflo ultrafilters, (Amicon). The concentrated pool (5 ml) was passed over a Sepharose CL-6B column (3×100 cm) at a flow rate of 10 ml/hr, for separation of PS antigen from C4BP in a running buffer of 0.05M Tris-HCl, 3M guanidine pH 6.0. The C4BP protein peak (15 ml) was dialyzed against TBS and the protein concentration was determined by measuring the optical density at 280 nm as described in Example 1. The C4BP was judged >95% pure with no detectable presence of protein S when analyzed by SDS-PAGE. The purified material represents approximately 10% of the total amount of C4BP in the starting material.

ii) Peptide Inhibition Assay

Each of the peptides produced as described in Example 1 and listed in Table 1 was analyzed for its ability to inhibit the binding of native protein S in liquid-phase to C4BP in solid-phase.

Microtiter wells of a 96 well plate were coated with 50 µl of 10 µg/ml purified C4BP in carbonate buffer (0.02M $Na_2CO_3$, pH 9.0, 0.02% Na-Azide). After blocking with 10% BSA in TBS, 50 µl of different concentrations of peptides diluted in washing buffer (TBS, 0.2% BSA, 5mM CaCl, 0.02% Tween 20) were separately admixed to C4BP-coated wells. After 2 hours at room temperature, 50 µl of a solution of biotinylated protein S, were admixed to each well to form a second binding admixture having a final concentration of 2 µg/ml. The plate was agitated and the samples were incubated 1 hour at room temperature. The samples were discarded and the wells were washed 3 times with washing buffer. To each well, 50 µl of strepavidin-alkaline-phosphatase (1 µg/ml washing buffer) were admixed and allowed to incubate for 30 minutes at room temperature. The strepavidin-alkaline-phosphatase was then discarded and the wells were washed 6 times with washing buffer.

The resulting optical densities of the reaction solutions were read as described before in Example 2C.

Results of the assay are reported as percent inhibition of C4BP binding. Percent of inhibition of C4BP binding is defined as:

$$I = 100\% - 100 \times (delta_T/delta_C)$$

where I is expressed as a percent; and
where 100%=delta/min of the amount of b-PS which specifically bound to C4BP-coated wells in the absence of any competing PS-peptide; and
where $delta_T$=the change in absorbance (405 nm) in the presence of competing PS-peptide; and
where $delta_C$=the change in absorbance (405 nm) in the absence of competing PS-peptide.

The results of the competition assays are shown in Table 2 and in FIGS. 1, 2, 3, and 4. The peptide designations corresponding to the SEQ ID NO are shown in Table 1. The results in Table 2 indicate that peptide PSP-12 was the strongest inhibitor, inhibiting the PS:C4BP complex formation by 80% at a peptide concentration of 800 μM. Peptides PSP-415* (4:1-15) PSP-417A (1:417-424), and PSP-430* (2:8-15) also inhibited the formation of PS:C4BP complex by nearly 80% at peptide concentrations of 800 μM. The peptides PSP-415*, PSP-417 (1:413-422), PSP-417P (1:413-424), and PSP-428* (2:4-15) each inhibited the PS:C4BP complex formation by approximately 60% at a peptide concentration of 800 μM. The peptide PSP-424 (1:421-427) inhibited the PS:C4BP complex formation by 40% at a concentration of 800 μM.

TABLE 2

| SEQ ID NO | AMINO ACID RESIDUE SEQUENCE | % INHIB. |
|---|---|---|
| (2:1-15) | SGIKEIIQEKQNKHC | 80 |
| (2:4-15) | KEIIQEKQNKHS | 55 |
| (2:8-15) | QEKQNKHS | 75 |
| (1:425-433)[1] | IIQEKQNKH | — |
| (1:421-427) | GIKEIIQ | 40 |
| (1:417-424) | QGASGIKE | 75 |
| (1:413-424) | NLMKQGASGIKE | 65 |
| (1:413-422) | NLMKQGASGI | 60 |
| (4:1-15) | DIRSWNLMKQGASGI | 80 |
| (4:1-11) | DIRSWNLMKQG | 60 |
| (4:1-8) | DIRSWNLM | — |
| (1:393-407)[1] | VESELIKPINPRLDG | — |
| (1:436-450)[1] | VIVVEKGSYYPGSGIA | — |
| (1:605-614)[1] | GVQLDLDEAI | 25 |

[1]The indicated polypeptides were synthesized as described in Example 1 and tested for capacity to inhibit PS binding to C4BP as described in Example 5Ai.

The peptides PSP-347 (1:347-361), PSP-32 (1:32-46), PSP-7 (1:187-200), PSP-417A (1:417-424), PSP-12 (1:420-434), and PSP-418* (4:1-15) all exhibited strong inhibition of PS:C4BP complex formation relative to PS-peptides from other regions of protein S. Additional PS peptides shown in Table 1 were also tested and shown to inhibit PS binding to C4BP. In subsequent experiments, the PSP-loop peptide (11:1-26) was shown to completely inhibit the binding of PS to C4BP at approximately 250 μM peptide concentration whereas PSP-12 did not result in complete inhibition at the same concentration. Peptides PSP-424K and PSP-428K exhibited similar inhibition profiles to that of PSP-12.

These data indicate that the peptides described above have the ability to inhibit PS binding to C4BP at the location or near the location of the PS:C4BP binding region. Based on these results, various minimum regions of PS were identified as significant sites for contact between PS and C4BP, and therefore define a PS polypeptide of this invention.

An alternative approach was used to test the ability of the peptides, PSP-loop, PSP-424K and PSP-428K, in comparison with that seen with the PSP-12 peptide, in inhibiting the binding of C4BP to PS. For this assay, the microtiter wells were coated with purified PS diluted to a concentration of 10 μg/ml in carbonate-coating buffer as described above. The wells were maintained to allow the PS to bind to the well walls. After the maintenance period, the wells were blocked also as described above. The selected PSP peptides were separately admixed at various concentrations ranging from 0–500 μM with biotinylated-C4BP (b-C4BP) at a concentration of 1 μg/ml. The admixtures were maintained on a fluid phase plate for 2 hours at room temperature to form peptide-C4BP complexes.

Fifty μl of the complexed admixtures were separately admixed to the prepared C4BP-coated wells and maintained for 1 hour at room temperature. Thereafter, the plate was washed and processed for developing as described above.

In this assay, the PSP-loop peptide inhibited the binding of b-C4BP to PS-coated wells with a half-maximal inhibitory concentration of approximately 15 μM ($IC_{50}$=15 μM) and a $IC_{90}$ of 50 μM. The other peptides, PSP-12, PSP-424K and PSP-428K, were also inhibitory but with an $IC_{50}$ of approximately 50 μM and an $IC_{90}$ of approximately 250 μM. Thus, the PSP-loop peptide (11:1-26) was more efficient at inhibiting the binding of C4BP to PS than the other three peptides tested.

iii) Antibodies that Inhibit Binding

Antibodies prepared in Example 2 immunoreactive with their respective immunizing peptides and which demonstrated immunoreactivity with purified protein S, were tested for the ability to inhibit protein S binding to immobilized C4BP using the ELISA system described in Example 5A with the following exceptions. Immunopurified polyclonal anti-peptide antibody (final concentration of 0 to 200 μg/ml (or 3.1 μM) was preincubated with 50 μl of biotinylated protein S (2 μg/ml), produced as described in Example 5Aii, for 1 hour at room temperature prior to addition onto C4BP-coated wells. Fifty μl of purified C4BP (10 μg/ml), produced as described in Example 5Ai, was coated and blocked to the wells as described in Example 5Aii. The remainder of the assay was performed as described in Example 5A. Results of the assay are reported as percent inhibition of C4BP binding. Percent of inhibition of C4BP binding is defined as:

$$I = 100\% - 100 \times (delta_T/delta_C)$$

where I is expressed as a percent; and
where 100%=delta/min of the amount of b-PS which specifically bound to C4BP-coated wells in the absence of any competing PS-peptide; and
where $delta_T$=the change in absorbance (405 nm) in the presence of competing antibody; and
where $delta_C$=the change in absorbance (405 nm) in the presence of competing antibody.

Figure 5:
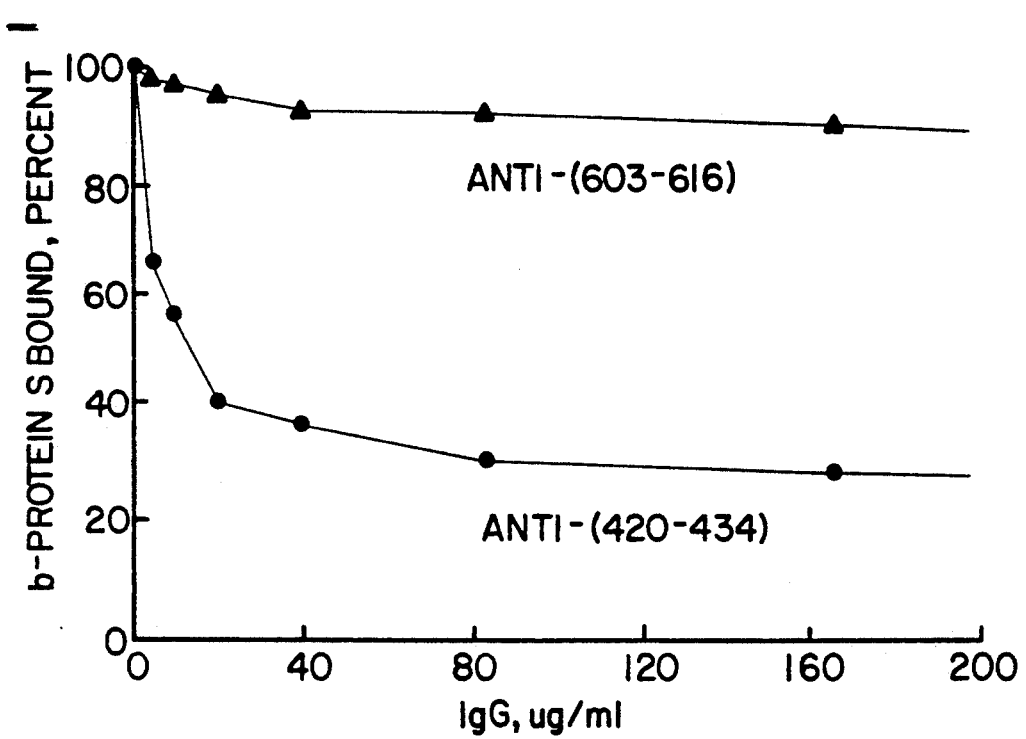
FIG. 5 illustrates the results of the Antibody Inhibition Assay described in Example 5Aiii. Varying concentrations of anti-PSP-12 (also referred to as anti-PS (420-434)) and anti-PSP-13 (also referred to as anti-PS (603-616)) antibody were incubated with the protein C4BP previously coated onto microtiter wells. Subsequently, biotinylated protein S (b-PS) was added to the wells and the amount of b-PS which bound to C4BP was detected as described in Example 2C.

The results of the antibody competition assays are shown in Table 3 and FIG. 5. The data from Table 3 indicates that polycolonal anti-PS(420-434) antibody was the only antibody that substantially inhibited the formation of PS:C4BP complex. Anti-PS(420-434) inhibited the binding of native protein S to C4BP by greater than 85% when present at a concentration of 3.1

μM. When the concentrations of anti-PS(420–434) (anti-PSP-12) and anti-PS(603–616) (anti-PSP-13*) were varied from 0–200 μg/ml, anti-PS(420–434) inhibition of PS:C4BP complex outperformed anti-PS(603–616) inhibition by approximately 60%. Anti-PS(420–434) inhibited PS:C4BP complex formation by 70% at a concentration of 200 μg/ml, where half of total inhibition occurred at a concentration of 5 μg/ml. Therefore, anti-PS(420–434) antibody binds native PS and inhibits PS binding to C4BP.

TABLE 3

| Polyclonal Antibody | % Inhibition |
|---|---|
| anti-PS(54–67) (anti-PSP-54) | 9 |
| anti-PS(561–574) (anti-PSP-561) | 5 |
| anti-PS(408–422) (anti-PSP-418*) | 12 |
| anti-PS(420–434) (anti-PSP-12) | 85 |
| anti-PS(603–616) (anti-PSP-13*) | 15 |
| anti-PS(621–635) (anti-PSP-14*) | 10 |

Thus a preferred anti-PS peptide antibody of this invention has the capacity to immunoreact with a PS peptide and to inhibit PS binding to C4BP. Screening for inhibition of PS binding to C4BP is conveniently done by the above inhibition assay.

An alternative approach was used to test the ability of the peptides, PSP-loop, PSP-424K and PSP-428K, in comparison with that seen with the PSP-12 peptide, in inhibiting the binding of PS to C4BP, the result of which was detected on polyclonal antibody-coated plates. For this assay, C4BP, biotinylated-PS (b-PS) and PSP peptides were admixed together at the respective concentrations of 3 μg/ml, 0.6 μg/ml and at a range of 0–500 μM (V:V:V). The admixtures were maintained for 2 hours at room temperature on a fluid phase plate to allow the binding and/or inhibition thereof of PS to C4BP by the PS-derived peptides. After the maintenance period, 50 μl of the admixture were separately admixed to wells previously coated with 10 μg/ml of anti-C4BP IgG polyclonal antibody. The admixtures were maintained for 1 hour at room temperature to allow for the binding of C4BP to C4BP-antibody-coated plates. The binding of biotinylated complexes to the antibody-coated plates was detected as described in Example 5Aii.

The PSP-loop peptide inhibited the binding of b-PS to C4BP (detected by the binding or inhibition of binding thereof to C4BP-antibody-coated plates) with an $IC_{50}$ of approximately 40 μM and an $IC_{90}$ of approximately 400 μM. The peptides, PSP-12 and PSP-424K, were also inhibitory but with lower effectiveness. Thus, the PSP-loop peptide was shown to efficiently inhibit the binding of PS to C4BP in the above-described antibody assay with comparable results to that shown in Example 5Aii in the peptide inhibition assay.

B. Epitope Mapping of Immunopurified Anti-PS(420–434)

In order to identify the epitopes of the anti-PS(420–434) antibody an ELISA assay was conducted using the peptides shown in Table 4. The peptides were coated and blocked to microtiter plates and incubated with concentrations of anti-PS(420–434) ranging from 0–5 μg/ml IgG according to the ELISA protocols previously described. The rest of the assay and the recording of data was performed as described in Example 2C.

TABLE 4

| Amino Acid Residue Sequence | | Binding Affinity |
|---|---|---|
| (1:420–434) | SGIKEIIQEKQNKHC | +++ |
| (2:1–15) | SGIKEIIQEKQNKHS | ++ |
| (1:434–420) | SHKNQKEQIIEKIGS | − |
| (3:1–15) | SGVKEIIQEKQNKHS | ++ |
| (2:4–15) | KEIIQEKQNKHS | ++ |
| (1:425–433) | IIQEKQNKH | − |
| (1:418–432) | GASGIKEIIQEKQNK | ++ |
| (1:413–427) | NLMKQGASGIKEIIQ | ++ |
| (1:421–427) | GIKEIIQ | − |
| (1:417–424) | QGASGIKE | ++ |
| (1:413–422) | NLMKQGASGI | − |
| (4:1–15) | DIRSWNLMKQGASGI | − |
| (4:1–11) | DIRSWNLMKQG | − |
| (4:1–8) | DIRSWNLM | − |

The results of the assay are shown in Table 4. The data indicates that anti-PS(420–434) bound with the highest affinity to peptides which contain the sequence -KEIIQ- (1:423–427) and had a length of more than 7 amino acid residues, or the sequence -QEKQNKHS- (1:427–434).

C. Competition Binding Assay Using PS in Solid Phase

Monoclonal antibodies, prepared in Example 4, immunoreactive with their respective immunizing peptides and which demonstrated immunoreactivity with purified protein S, were tested for the ability to inhibit C4BP binding to immobilized PS in the ELISA system described in Example 2C with the following exceptions. Immunopurified anti-PS(420–434) monoclonal antibody, designated MAb 56, in varying ranges from 0–150 μg/ml were preincubated with immobilized protein S for 2 hours at room temperature. Biotinylated C4BP (b-C4BP), produced by combining biotin (Clontech) with C4BP and following the manufacturer's instructions, was admixed to the wells in a final concentration of 1 μg/ml and maintained for 1 hour at room temperature. The rest of the assay and the recording of data was as described in 2C.

The results show a substantial decrease in the formation of b-C4BP:PS complex with increasing concentration of MAb 56, compared to the control nonimmune IgG. Therefore, the MAb 56 inhibits the binding of C4BP to PS.

An alternative approach was used to test the ability of the peptides, PSP-loop, PSP-424K and PSP-428K, in comparison with that seen with the PSP-12 peptide, in inhibiting the binding of PS to C4BP, the result of which was detected on monoclonal antibody-coated plates. For this assay, biotinylated-C4BP (b-C4BP), PS and PSP peptides were admixed together at the respective concentrations of 0.5 μg/ml, 1.0 μg/ml and at a range of 0–500 μM (V:V:V). The admixtures were maintained for 2 hours at room temperature on a fluid phase plate to allow the binding and/or inhibition thereof of PS to C4BP by the PS-derived peptides. After the maintenance period, 50 μl of the admixture were separately admixed to wells previously coated with 10 μg/ml of MAb S-7 (ATCC No. HB 80819). The admixtures were maintained for 1 hour at room temperature to allow for the binding of C4BP to MAb S-7-antibody-coated plates. The binding of biotinylated complexes to the antibody-coated plates was detected as described in Example 5Aii.

The PSP-loop peptide inhibited the binding of b-PS to C4BP (detected by the binding or inhibition of binding thereof to MAb S-7-antibody-coated plates) with an $IC_{50}$ of approximately 35 μM and an $IC_{90}$ of approximately 100 μM. the peptides, PSP-12 and PSP-424K, were also inhibitory but with lower effectiveness having an $IC_{50}$ of approximately 50 μM and an $IC_{90}$ of approximately 250 μM. Thus, the PSP-loop peptide was shown to efficiently inhibit the binding of PS to C4BP in the above-described antibody assay with comparable results to that shown in Example 5Aiii with assay using anti-C4BP polyclonal antibody and in Example 5Aii in the peptide inhibition assay.

6. Immunoassays to Detect Free Protein S ($PS_F$)

A. ELISA with Anti-$PS_T$ in Solid Phase

For the assays described below, $PS_T$ is defined as "total" protein S whether it is found in solid or liquid-phase. $PS_T$ includes protein S complexed to any other protein including C4BP, or protein S free of any other protein. $PS_F$ is defined as protein S free of complexation with C4BP, and which is capable of and available for complexation with C4BP.

A monoclonal antibody was prepared as described in Example 4, but using purified protein S as the immunogen. The Mab was screened using the methods of Example 4 for its ability to bind protein S complexed to C4BP. The resultant Mab with the desired characteristics was designated LJS S-7 (or MAb S-7) (ATCC #HB 10819). Purified MAb S-7 is coated to wells of microtiter plates and blocked as described in Example 3. To the MAb S-7 containing wells, 50 μl/well serial dilutions (1:500 to 1:64,000) of purified protein S is admixed to produce a standard concentration curve. In addition, serial dilutions 1:2,000-1:4,000 of donor blood in washing buffer is admixed to separate wells that are similarly coated. After a 2 hour incubation at room temperature, the standards and the sample dilutions are removed. Next, biotinylated MAb S-7, formed by the methods described in 5A, are admixed to each well, and the rest of the assay is performed as described in Example 2C to detect immunoreacting products containing free PS. The normal human plasma concentrations of C4BP and $PS_T$ were measured at 155 μg/ml (270 nM) and 26 μg/ml (350 nM), respectively.

The results indicate that immobilized MAb S-7 captures total PS, and thereafter the $PS_F$ is detected in the captured PS population by the use of the $PS_F$-specific antibody, MAb 56. Thus, this approach allows for the detection of $PS_F$ in fluid samples.

B. Assay for $PS_F$ using Anti-$PS_F$ in Solid Phase

To show that MAb 56 recognizes only free protein S and is useful for selective capture of free protein S, solid phase MAb 56 was prepared and free PS was immunoabsorbed from normal human plasma. To that end, monoclonal antibody MAb 56 prepared in Example 4, was coupled to activated CNBr-sepharose 4B (Pharmacia) following the manufacturer's instructions (3 mg of IgG/ml gel). Next, 400 μl of normal human plasma (George King Inc., Overland Kans.)) was maintained with 100 μl of wet beads containing the immobilized monoclonal antibody MAb 56 in TBS buffer for 90 minutes at 8° C. under continuous stirring. The plasma/antibody MAb 56 admixture was centrifuged at 3000 rpm at 8° C. The supernatant was then aliquoted and frozen at −70° C. for subsequent analysis. Two other plasma samples were used as controls in the above adsorption method to analyze the specificity of the MAb 56 treatment. For one sample, an identical 400 μl normal plasma aliquot was maintained under the same conditions without sepharose. For another sample, 400 μl of normal human plasma was incubated with 100 μl of MAb S-7 anti-$PS_T$ coupled to sepharose beads under the same conditions. The MAb S-7 recognizes both complex and free protein S, and previously was shown to adsorb all protein S antigen from plasma.

To visually identify free and complexed protein S in the various adsorbed fractions produced above, two-dimensional rocket crossed immunoelectrophoresis (CIEP) was performed as described by Laurell et al., *Anal. Biochem.*, 10:358–361 (1985). First 30 μl of either treated plasma, or a control plasma that was not exposed to sepharose, was loaded on a gel containing 1% agarose, 0.3 mM/L EDTA in Tris-glycine buffer, pH 8.7. The gel was poured on a Gel-Bond film partially covered with a piece of metal device to preserve an area for the agarose used for the second dimension of electrophoresis. Electrophoresis in the first dimension was conducted at 4° C. at 1 mA/cm for 45 min. After completion of the electrophoresis in the first dimension, the gel for the second dimension containing 5 mmol/L EDTA, 3% polyethylenglycol, and goat anti-PS antiserum at a dilution 1/400, Was applied. The electrophoresis in the second dimension was performed at 22° C. and 1 2 mA/cm for 18 hours. The plates were washed, dried and stained as described by Laurell et al., supra.

Figure 6A:
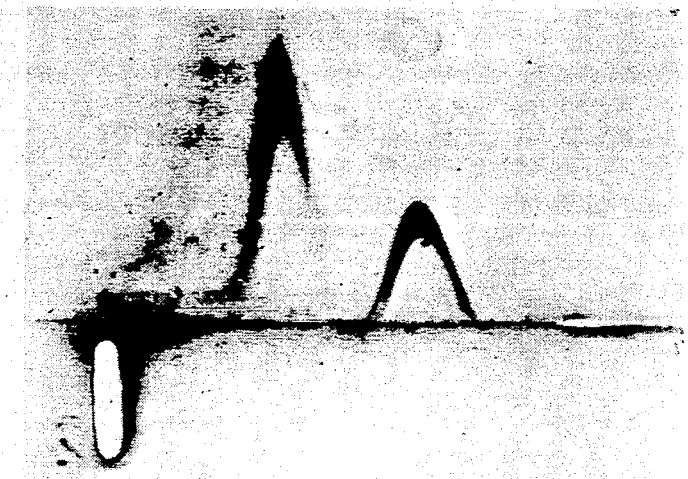
FIG. 6A shows the results the control normal plasma sample where the large laurell rocket represents the C4BP:PS complex and the small laurell rocket represents free protein S.
Figure 6B:
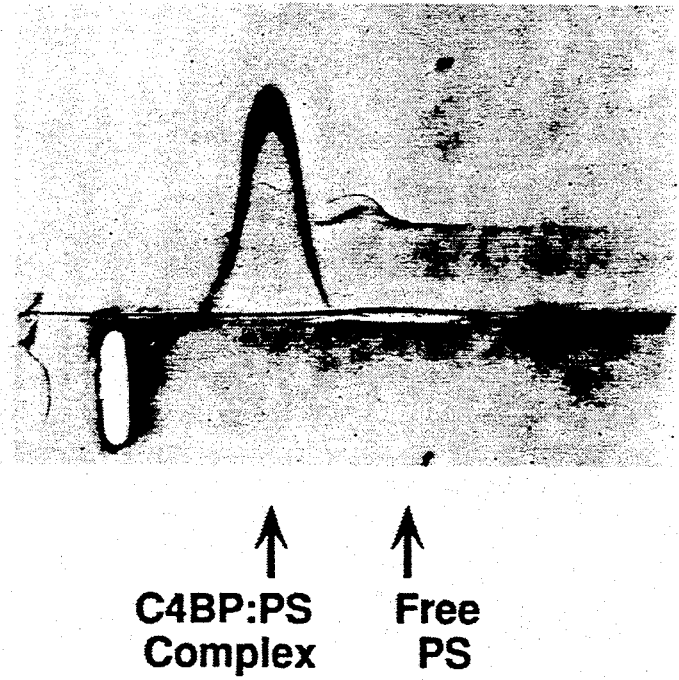
FIG. 6B shows the results of a plasma sample adsorbed with MAb 56 where the single laurell rocket represents the C4BP:PS complex.

The results of the 2-D electrophoresis are shown in FIG. 6, revealed the lack of the $PS_F$ band at the expected location for MAb 56 adsorbed plasma (compared to the $PS_F$ band location for untreated plasma). In addition, the C4BP:PS complex produced a band at the expected location for the MAb 56 adsorbed plasma. Therefore, the MAb 56 specifically binds to protein S species that is not complexed to C4BP, i.e., is free PS.

Alternatively, to identify polyclonal rabbit anti-PS(420–434) antibodies that only recognize free protein S, 3 mg of immunoaffinity purified anti-PS(420–434) antibody, prepared in Example 3, was coupled to 1 ml of resuspended CNBr-sepharose 4B (Pharmacia) according to the manufacturer's instructions. After blocking the beads with 0.1M ethanolamine pH 9.0, the beads were poured in a chromatography column (1×1 cm) which was equilibrated in TBS buffer at room temperature.

To the anti-PS(420–434)-containing column, different mixtures of complexed and free protein S, prepared as described in Examples 2C and 5A were passed through at a flow of 1 ml/min. After washing with 50 ml of TBS buffer, the column was eluted with 10 ml of 3M thiocyanate in TBS buffer. The eluted fractions were dialyzed in TBS buffer and the resulting samples were subjected to SDS-PAGE using 4–15% gradient gels. The gels were stained with silver in order to analyze the different bands of proteins, or transferred to nitrocellulose paper and subjected to immunoblotting with a specific antibody against protein S or C4BP. As a control, another affinity column with different goat polyclonal anti-PS antibodies coupled to sepharose was used to adsorb all protein S.

Figure 7:
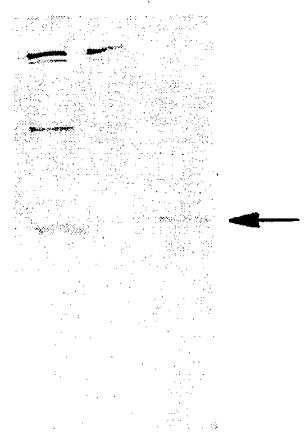
FIG. 7 illustrates the results of the SDS-PAGE described in the assay for free protein S by adsorption using anti-PS(420-434) polyclonal antibodies as described in Example 6B. Lane 1 corresponds to the starting material containing both free PS and the PS:C4BP complex. Lane 2 corresponds to the flow-through of the starting material after passage through a column contain anti-PS(420-434) polyclonal antibody in solid phase. Lane 3 corresponds to the fraction of the starting material eluted from the column with 3M thiocyanate. The arrow indicates the location of the band corresponding to free protein S.

The results, shown in FIG. 7, show that only free protein S was eluted from the column. This indicates that polyclonal anti-PS(420–434) only binds to free protein S and will not bind to the PS:C4BP complex.

These results also show that the anti-$PS_F$ antibodies of this invention are useful to purify free PS from complex biological fluids such as blood, plasma and plasma derived products.

7. Immunoassay to Detect Competent C4BP Using PSP-12) Peptide

A. Binding of C4BP to Immobilized PSP-12)

Fifty μl of synthetic peptide PSP-12 (20 μM) or the native protein S (10 μg/ml) diluted in 0.02M Na2CO3 buffer pH 9.0 were separately coated on microtiter wells for 1 hour at 37° C. The incubation sample was discarded and the wells were blocked with 200 μl of 10% BSA in 0.05M Tris-HCl, 0.1M NaCl, pH 7.4 (TBS) and stored at 4° C. until used. The wells were then washed 3 times with 0.2% BSA in TBS, 5 mM Ca++ and 0 02% Tween-20 (washing buffer). After the washing, 50 μl serial dilutions of biotinylated C4BP (b-C4BP) in concentrations ranging from 0–20 μg/ml were admixed to each well. The solution was maintained for 2 hours at room temperature to allow C4BP to complex with (bind to) the PS or PSP-12 in the wells. The rest of the assay was performed as described in Example 2C. The results indicated that the peptide PSP-12 and purified PS bind C4BP at the same level.

B. C4BP Immunocapture Assay

In order to detect competent C4BP present in a vascular fluid sample, microtiter wells are coated with the peptide PSP-12 and blocked as described in section 7A.

To the PSP-12-coated wells, 50 μl/well serial dilutions of purified C4BP (1:500 to 1:64,000) prepared as in Example 5A or NHP (1:2,000–1:4,000 dilutions of unknown samples) in washing buffer are admixed to each of the wells. After 1 hour incubation at room temperature, the standards and the sample dilutions are removed and the wells are washed 3 times with washing buffer. Next, immunoaffinity purified rabbit anti-C4BP polyclonal antibodies (10 μg/ml) are added to each well. After 1 hour incubation at room temperature the polyclonal antibodies are removed by washing with washing buffer. This step is followed by another hour of incubation with 50 μl/well of biotinylated goat anti-rabbit IgG (1 μg/ml). Next, 1 μg/ml of alkaline phosphatase conjugated strepavidin (SAAP) (50 μl/well) is admixed to each well and maintained for 30 minutes at room temperature. The SAAP is removed and the wells are washed 6 times with washing buffer. Five mg/ml of PNPP (100 μl/well) in 0.1M diethylamine/HCl buffer, pH 9.0, is then admixed to each well. The change in absorbance at 405 nm is measured using EL 312 Microplate reader (BIO-TEK Instruments Inc., Winooski, Vt.) and the data are analyzed using a kinetic program software package (Kinetiacalc, Bio-tek). The results show binding in the control positive wells only and also in the lower dilutions of NHP indicating capture of the C4BP.

C. C4BP Monoclonal Immunocapture Assay

Purified monoclonal antibodies against the α chain of C4BP (available from Biodesign International Kennebunkport, Me.) (10 μg/ml) in 50 μl 0.02M Na2CO3 buffer, pH 9.0, are coated on wells of microtiter plates for 1 hour at 37° C. The wells are blocked with 200 μl of 10% BSA in TBS and stored at 4° C. until use. Prior to use, the wells are washed three times with 0.2% BSA in TBS, 5 mM Ca++, 0.02% sodium azide and 0.02% Tween-20 (washing buffer). Serial dilutions from 1:500 to 1:64,000 in 50 μl/well of purified C4BP or NHP are admixed to produce a standard concentration curve. In addition, serial dilutions 1:2,000–1:4,000 of unknown normal human plasma samples in washing buffer are admixed to the wells. After 1 hour incubation at room temperature, the standards and the sample dilutions are removed and the wells are washed 3 times with washing buffer.

Next, synthetic b-PSP-12 is diluted to concentrations (0–200 μM) in washing buffer and is incubated in the wells containing C4BP bound to anti-C4BP polyclonal antibodies for 1 hour at room temperature. The remainder of the assay is performed as described in Example 2C. The results show binding in the control positive wells only and in the lower dilutions of NHP indicating capture of b-PSP-12.

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposit of materials therein does not constitute an admission that the written description herein contained is inadequate to enable the practice of any aspect of the invention, including the best mode thereof, nor are the deposits to be construed as limiting the scope of the claims to the specific illustrations that they represent. Indeed, various modifications of the invention in addition to those shown and described herein will becomes apparent to those skilled in the art from the foregoing description and fall within the scope of the appended claims.

What is claimed is:

1. A protein S polypeptide having a length of from about 7 to no more than 100 amino acid residues, said polypeptide including an amino acid residue sequence represented by the formula: -KEIIQ-, said sequence shown in SEQ ID NO 1 from residue 423 to residue 427, said polypeptide further having a sequence that corresponds to residue 327 to residue 323 of the sequence of protein S shown in SEQ ID NO 1, and wherein said polypeptide inhibits binding of protein S to C4b binding protein.

2. The polypeptide of claim 1 wherein said polypeptide includes an amino acid residue sequence represented by the formula: -KEIIQEKQNKH-, said sequence shown in SEQ ID NO 1, from residue 423 to residue 433.

3. The polypeptide of claim 2 wherein said polypeptide has an amino acid residue sequence, the SEQ ID NO and corresponding residues of which are shown in parenthesis, represented by a formula selected from the group consisting of:

| | |
|---|---|
| SGIKEIIQEKQNKHC, | (1:420–434) |
| SGIKEIIQEKQNKHS, | (2:1–15) |
| SGVKEIIQEKQNKHS, | (3:1–15) |
| KEIIQEKQNKHS, and | (2:4–15) |
| CIRSWNLMKQGASIKEIIQEKQNKHC | (11:1–26). |

4. A protein S polypeptide having an amino acid residue sequence, the SEQ ID NO and corresponding residues of which are shown in parenthesis, represented by a formula selected from the group consisting of:

| | |
|---|---|
| CPEGYRYNLKSKSC, | (1:187–200) |
| SPEGYRYNLKSKSSE | (5:1–15) |
| VEELEHSISIKIAKE | (1:347–361) |
| QGASGIKE, | (1:417–424) |
| NLMKQGASGIKE | (1:413–424) |
| NLMKQGASGI | (1:413–422) |
| CIRSWNLMKQGASGI | (1:408–422) |
| DIRSWNLMKQGASGI | (4:1–15) |
| DIRSWNLMKQG | (4:1–11) |
| CIRSWNLMKQGASIKEIIQEKQNKHC | (11:1–26) |
| SGIKEIIQEKQNKHC, | (1:420–434) |
| SGIKEIIQEKQNKHS, | (2:1–15) |
| SGVKEIIQEKQNKHS, | (3:1–15) |
| SGIKKIIQEKQNKL, | (12:1–14) |
| SGIKEIIQKKQNKC, | (13:1–14) |
| KEIIQEKQNKHS, | (2:4–15) |
| GASGIKEIIQEKQNK, | (1:418–432) |
| NLMKQGASGIKEIIQ, | (1:413–427) |
| GIKEIIQ, and | (1:421–427) |
| QEQNKHS, | (1:427–434) | and wherein said polypeptide inhibits binding of protein S to C4B binding protein.

* * * * *

UNITED STATES PATENT AND TRADEMARK OFFICE
CERTIFICATE OF CORRECTION

PATENT NO. : 5,321,123

DATED : June 14, 1994

INVENTOR(S) : Griffin, et al.

It is certified that error appears in the above-identified patent and that said Letters Patent is hereby corrected as shown below:

In column 55, line 62, correct as follows:

Please delete "323" and replace with --523--.

Signed and Sealed this

Eighteenth Day of October, 1994

Attest:

BRUCE LEHMAN

Attesting Officer

Commissioner of Patents and Trademarks